United States Patent
Sarkisian et al.

(10) Patent No.: US 12,048,668 B2
(45) Date of Patent: Jul. 30, 2024

(54) SELF-ALIGNING MECHANISMS IN PASSIVE AND POWERED EXOSKELETONS

(71) Applicant: UNIVERSITY OF UTAH RESEARCH FOUNDATION, Salt Lake City, UT (US)

(72) Inventors: Sergei V. Sarkisian, Midvale, UT (US); Tommaso Lenzi, Salt Lake City, UT (US); Dante Amico Bennett Archangeli, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 37 days.

(21) Appl. No.: 17/911,526

(22) PCT Filed: Mar. 19, 2021

(86) PCT No.: PCT/US2021/023231
§ 371 (c)(1),
(2) Date: Sep. 14, 2022

(87) PCT Pub. No.: WO2021/188947
PCT Pub. Date: Sep. 23, 2021

(65) Prior Publication Data
US 2023/0007984 A1    Jan. 12, 2023

Related U.S. Application Data

(60) Provisional application No. 62/992,631, filed on Mar. 20, 2020.

(51) Int. Cl.
*A61H 3/00* (2006.01)
*A61H 1/02* (2006.01)
*B25J 9/00* (2006.01)

(52) U.S. Cl.
CPC ............... *A61H 3/00* (2013.01); *A61H 1/024* (2013.01); *A61H 1/0244* (2013.01);
(Continued)

(58) Field of Classification Search
CPC ........ A61H 1/02; A61H 1/0237; A61H 1/024; A61H 1/0244; A61H 1/0262;
(Continued)

(56) References Cited

U.S. PATENT DOCUMENTS 4,407,496 A   10/1983   Johnson
4,483,194 A   11/1984   Rudolf
(Continued)

FOREIGN PATENT DOCUMENTS

CN    101336849 A    1/2009
CN    102204918 A    10/2011
(Continued)

OTHER PUBLICATIONS

Beil, Jonas, and Tamim Asfour. "New mechanism for a 3 DOF exoskeleton hip joint with five revolute and two prismatic joints." 2016 6th IEEE International Conference on Biomedical Robotics and Biomechatronics (BioRob). IEEE, 2016.
(Continued)

*Primary Examiner* — Colin W Stuart
*Assistant Examiner* — Douglas Y Sul
(74) *Attorney, Agent, or Firm* — Workman Nydegger

(57) ABSTRACT

An exoskeleton device that includes an artificial joint and a frame member extending from the artificial joint. The frame member is configured for extension over a limb of a user. The exoskeleton device also includes a self-aligning mechanism connected to the frame member. The self-aligning mechanism includes three passive degrees of freedom (pDOF) provided in a prismatic-revolute-revolute (PRR) configuration. The self-aligning mechanism also includes a limb attachment member configured for mechanically coupling to a portion of the limb of the user.

17 Claims, 14 Drawing Sheets

(52) U.S. Cl.
CPC ....... B25J 9/0006 (2013.01); *A61H 2003/007* (2013.01); *A61H 2201/123* (2013.01); *A61H 2201/1436* (2013.01); *A61H 2201/164* (2013.01); *A61H 2201/165* (2013.01); *A61H 2201/1673* (2013.01)

(58) Field of Classification Search
CPC .............. A61H 2001/0207; A61H 3/00; A61H 2201/1215; A61H 2201/123; A61H 2201/1238; A61H 2201/164; A61H 2201/1642; A61H 2201/165; A61H 2201/1676; A61H 2201/5061; A61H 2201/5079; A61H 2205/10; A61F 5/0123
See application file for complete search history.

(56) References Cited

U.S. PATENT DOCUMENTS

| | | | |
|---|---|---|---|
| 4,762,006 | A | 8/1988 | Asakawa et al. |
| 4,772,928 | A | 9/1988 | Dietrich et al. |
| 5,027,657 | A | 7/1991 | Juckenack et al. |
| 5,998,742 | A | 12/1999 | Liu et al. |
| 6,166,013 | A | 12/2000 | Coghlan et al. |
| 6,237,399 | B1 | 5/2001 | Shivaram et al. |
| 6,829,510 | B2 | 12/2004 | Nathan et al. |
| 7,279,010 | B2 | 10/2007 | Cheng |
| 7,347,954 | B2 | 3/2008 | Banno et al. |
| 7,437,954 | B2 | 10/2008 | Sakano |
| 7,485,152 | B2 | 2/2009 | Haynes et al. |
| 8,087,498 | B2 | 1/2012 | Dupuis et al. |
| 8,500,823 | B2 | 8/2013 | Herr et al. |
| 8,696,764 | B2 | 4/2014 | Hansen et al. |
| 8,800,366 | B2 * | 8/2014 | Scott ..................... A61H 1/0274 600/595 |
| 8,870,967 | B2 | 10/2014 | Herr et al. |
| 8,974,543 | B2 | 3/2015 | Balboni et al. |
| 9,089,443 | B2 | 7/2015 | Nakaya et al. |
| 9,101,451 | B2 | 8/2015 | Chugunov |
| 9,717,606 | B2 | 8/2017 | Gramnaes |
| 9,770,347 | B2 | 9/2017 | Shen |
| 9,808,357 | B2 | 11/2017 | Langlois |
| 10,335,291 | B2 | 7/2019 | Djian et al. |
| 10,342,681 | B2 | 7/2019 | Herr et al. |
| 2002/0147336 | A1 | 10/2002 | Liu et al. |
| 2003/0104365 | A1 | 6/2003 | Gurney et al. |
| 2004/0121407 | A1 | 6/2004 | Distefano et al. |
| 2005/0080061 | A1 | 4/2005 | Belanoff |
| 2007/0225620 | A1 * | 9/2007 | Carignan ............... B25J 17/025 601/5 |
| 2008/0287834 | A1 | 11/2008 | Pusch |
| 2009/0088425 | A1 | 4/2009 | Bailly et al. |
| 2009/0229378 | A1 | 9/2009 | Kurtz et al. |
| 2010/0169988 | A1 | 7/2010 | Kohli et al. |
| 2012/0028358 | A1 | 2/2012 | Solodushko et al. |
| 2013/0319135 | A1 | 12/2013 | Okada et al. |
| 2014/0276261 | A1 | 9/2014 | Caires et al. |
| 2015/0105782 | A1 | 4/2015 | D'Lima et al. |
| 2016/0041149 | A1 | 2/2016 | Lindquist et al. |
| 2016/0158029 | A1 | 6/2016 | Kuiken et al. |
| 2016/0242936 | A1 | 8/2016 | Goldfarb et al. |
| 2016/0296346 | A1 | 10/2016 | Burke et al. |
| 2016/0331560 | A1 | 11/2016 | Tong et al. |
| 2017/0128312 | A1 | 5/2017 | Park et al. |
| 2018/0116828 | A1 | 5/2018 | Quinn et al. |
| 2018/0147073 | A1 | 5/2018 | Ly et al. |
| 2018/0194000 | A1 | 7/2018 | Smith et al. |
| 2018/0256372 | A1 | 9/2018 | Boiten et al. |
| 2018/0325766 | A1 | 11/2018 | Arzanpour et al. |
| 2018/0327373 | A1 | 11/2018 | Yang et al. |
| 2019/0020934 | A1 | 1/2019 | Goyal et al. |
| 2019/0111299 | A1 | 4/2019 | Radcliffe et al. |
| 2019/0160653 | A1 | 5/2019 | Lee et al. |
| 2019/0209348 | A1 | 7/2019 | Casler et al. |
| 2019/0314978 | A1 * | 10/2019 | Hunt ..................... B25J 9/0006 |
| 2020/0038279 | A1 * | 2/2020 | Sarakoglou ............... A61H 3/00 |
| 2021/0053208 | A1 * | 2/2021 | Paine ................... A61H 1/0244 |
| 2021/0161748 | A1 * | 6/2021 | Kim ..................... A61H 1/0277 |
| 2021/0247249 | A1 | 8/2021 | Lenzi et al. |
| 2021/0338458 | A1 | 11/2021 | Lenzi et al. |
| 2022/0401284 | A1 * | 12/2022 | Arzanpour ............. B25J 9/0006 |

FOREIGN PATENT DOCUMENTS

| | | |
|---|---|---|
| CN | 103271783 A | 9/2013 |
| CN | 108836583 A | 11/2018 |
| CN | 109044742 A | 12/2018 |
| CN | 209695751 U | 11/2019 |
| CN | 111110520 A | 5/2020 |
| DE | 4016147 A1 | 11/1991 |
| EP | 0795741 A2 | 9/1997 |
| EP | 1933775 A2 | 6/2008 |
| EP | 2178680 A2 | 4/2010 |
| GB | 2302949 A | 2/1997 |
| KR | 10-2017-0111255 A | 10/2017 |
| WO | 2007/027668 A2 | 3/2007 |
| WO | 2009/015751 A1 | 2/2009 |
| WO | 2009/016478 A2 | 2/2009 |
| WO | 2016/094413 A1 | 6/2016 |
| WO | 2017/059115 A1 | 4/2017 |
| WO | 2018/087997 A1 | 5/2018 |

OTHER PUBLICATIONS

Beil, Jonas, Charlotte Marquardt, and Tamim Asfour. "Self-aligning exoskeleton hip joint: kinematic design with five revolute, three prismatic and one ball joint." 2017 International Conference on Rehabilitation Robotics (ICORR). IEEE, 2017.

International Search Report and Written Opinion dated Nov. 14, 2019 for PCT/US2019/048489.

International Search Report and Written Opinion received for PCT Patent Application No. PCT/US19/47536, mailed on Nov. 20, 2019, 8 pages.

International Search Report and Written Opinion received for PCT Patent Application No. PCT/US19/48489, mailed on Nov. 14, 2019, 8 ages.

International Search Report and Written Opinion received for PCT Patent Application No. PCT/US2020/000009, mailed on Feb. 9, 2021, 16 pages.

International Search Report and Written Opinion received for PCT Patent Application No. PCT/US21/23231, mailed on Jun. 14, 2021, 7 pages.

Leisle et al., "Cellular encoding of Cy dyes for single-molecule imaging", Elite vol. 5, 2016, pp. e19088.

Lenzi et al., "Actively variable transmission for robotic knee prostheses", 2017 IEEE International Conference on Robotics and Automation (ICRA), IEEE, May 29, 2017 (May 29, 2017), pp. 6665-6671.

Liu et al., "Imaging Live-Cell Dynamics and Structure at the Single-Molecule Level", Mol. Cell., vol. 58 No. 4, 2015, pp. 644-659.

Peng et al., "Site-specific bioorthogonal labeling for fluorescence imaging of intracellular proteins in living cells", J. Am. Chem. Soc., vol. 138, No. 43, 216, pp. 14423-14433.

Syed et al., "Expanding the Zebrafish Genetic Code through Site-Specific Introduction of Azido lysine", Bicyclononyne-lysine, and Diazirine-lysine. Int. J. Mol. Sci., vol. 20, No. 10, May 2019, pp. 2577.

Written Opinion received for PCT Patent Application No. PCT/US2020/000009, mailed on Jul. 22, 2020, 6 pages.

Supplementary European Search Report received for EP Patent Application No. 21770510.2, mailed on Feb. 6, 2024, 11 pages.

\* cited by examiner

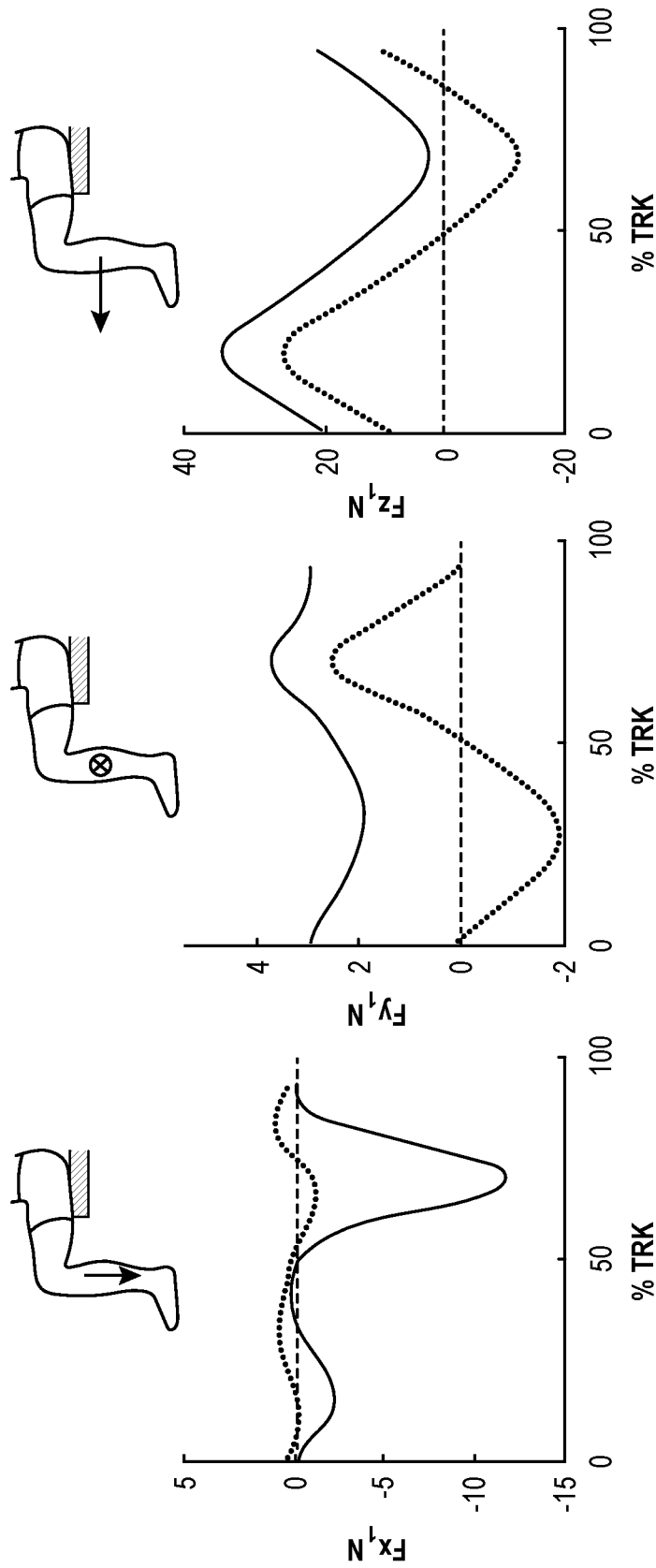

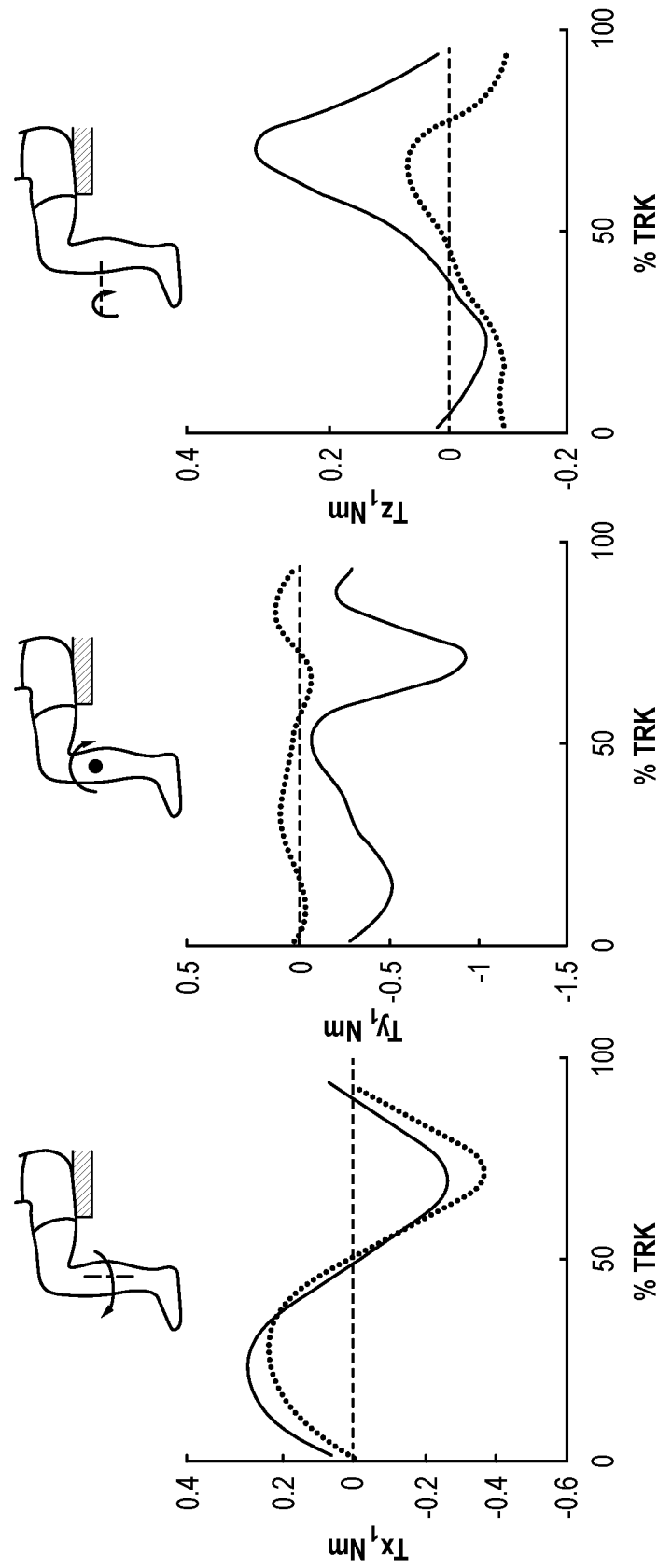

SELF-ALIGNING MECHANISMS IN PASSIVE AND POWERED EXOSKELETONS

CROSS-REFERENCE TO RELATED APPLICATIONS

This patent application is a nationalization of and claims priority to PCT Application No. PCT/US2021/023231 filed on Mar. 19, 2021 and titled "SELF-ALIGNING MECHANISMS IN PASSIVE AND POWERED EXOSKELETONS", which claims priority to and the benefit of U.S. Provisional Patent Application Ser. No. 62/992,631, filed Mar. 20, 2020 and titled "SELF-ALIGNING MECHANISMS IN PASSIVE AND POWERED ORTHOSES". Each of the aforementioned applications is incorporated by reference herein in their entirety.

STATEMENT REGARDING FEDERALLY SPONSORED RESEARCH

This invention was made with government support under W81XWH-16-1-0701 awarded by the Medical Research and Development Command. The government has certain rights in the invention.

BACKGROUND

Exoskeletons, such as powered exoskeletons, are used for various purposes, such as rehabilitation, assistance, strength amplification, productivity enhancement, and/or others. Powered exoskeletons operate by transmitting a controlled amount of torque to the wearer's body. However, transmitting torque to the wearer's body in a safe, comfortable, and/or effective manner is associated with many challenges. For example, high variability exists anatomical measurements and proportions between different humans. Furthermore, the shape and/or volume of human limbs varies with muscle activation and physical interaction with exoskeletons. A particular challenge in the effective implementation of exoskeletons is associated with aligning rotational and/or translational axes of exoskeletons (e.g., artificial joints) with anatomical rotational and/or translational axes of human users (e.g., anatomical joints).

Misalignments between artificial joints and anatomical joints may result in spurious forces and/or torques applied to the user. Spurious forces and/or torques may in turn produce unwanted load on the anatomical joints and/or shear stress on the user's skin. Such unwanted load and/or shear stress can reduce user comfort and/or user safety when operating an exoskeleton.

Accordingly, there is an ongoing need for mechanisms capable of improving exoskeletons. In particular, there is an ongoing need for mechanisms that can effectively align anatomical joints with artificial joints of exoskeletons. The subject matter claimed herein is not limited to embodiments that solve any disadvantages or that operate only in environments such as those described above. Rather, this background is only provided to illustrate one exemplary technology area where some embodiments described herein may be practiced.

SUMMARY

Disclosed herein are self-aligning mechanisms that may be utilized in exoskeletons (powered or non-powered) to dynamically align anatomical and exoskeleton joints. An exoskeleton including the self-aligning mechanisms can be configured to adjust to individual user's unique kinesiology and motion to avoid or reduce uncomfortable or injurious spurious forces and/or torques to the user.

The self-aligning mechanisms use a combination of prismatic and revolute passive degrees of freedom and/or elastic elements to dynamically align the anatomical and artificial joint. The self-aligning mechanism is added in series into the human-robot kinematic chain. These self-aligning mechanisms may be utilized in passive or powered exoskeletons (or orthoses), such as a powered hip exoskeleton or a powered knee exoskeleton.

The self-aligning mechanisms beneficially function to provide dynamic alignment of the actuated and anatomical axis in a manner that accounts for variations in user anthropometry, while also beneficially minimizing stress on the user's joint and soft tissues. The self-aligning mechanisms are configured to transmit torque to the intended joint while reducing undesired loads on the limb.

The self-aligning mechanisms described herein allow for dynamic alignment of the actuated and anatomical axis for various types of user anatomies. This allows for exoskeletons with reduced need of customization and potentially less weight due to the decreased need for individual customization features.

Some embodiments provide an exoskeleton device that includes an artificial joint and a frame member extending from the artificial joint. The frame member is configured for extension over a limb of a user. The exoskeleton device also includes a self-aligning mechanism connected to the frame member. The self-aligning mechanism includes three passive degrees of freedom (pDOF) provided in a prismatic-revolute-revolute (PRR) configuration. The self-aligning mechanism also includes a limb attachment member configured for mechanically coupling to a portion of the limb of the user.

Some embodiments provide a method for facilitating exoskeleton-assisted movement. The method includes arranging an exoskeleton device on a user limb with an artificial joint of the exoskeleton device positioned about a joint of the user limb. The method also includes applying a force to a first portion and a second portion of the user limb with the exoskeleton device. The first portion and the second portion of the user limb are on opposing longitudinal sides of the joint of the user limb. Furthermore, the method includes compensating for misalignment between the artificial joint and the joint of the user limb with a self-aligning mechanism of the exoskeleton device. The self-aligning mechanism is positioned about the first portion of the user limb, and the self-aligning mechanism includes three passive degrees of freedom (pDOF) provided in a prismatic-revolute-revolute (PRR) configuration. The compensation contributes to reduced spurious forces and/or torques exerted on the first portion of the user limb by the exoskeleton device.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered limiting in scope, embodiments will be described and explained with additional specificity and detail through the use of the accompanying drawings.

FIGS. 6A-9 illustrate graphs of forces and torques applied to a portion of a user's limb by exoskeleton devices when using a self-aligning mechanism and when not using a self-aligning mechanism;

DETAILED DESCRIPTION

Overview

Figure 1:
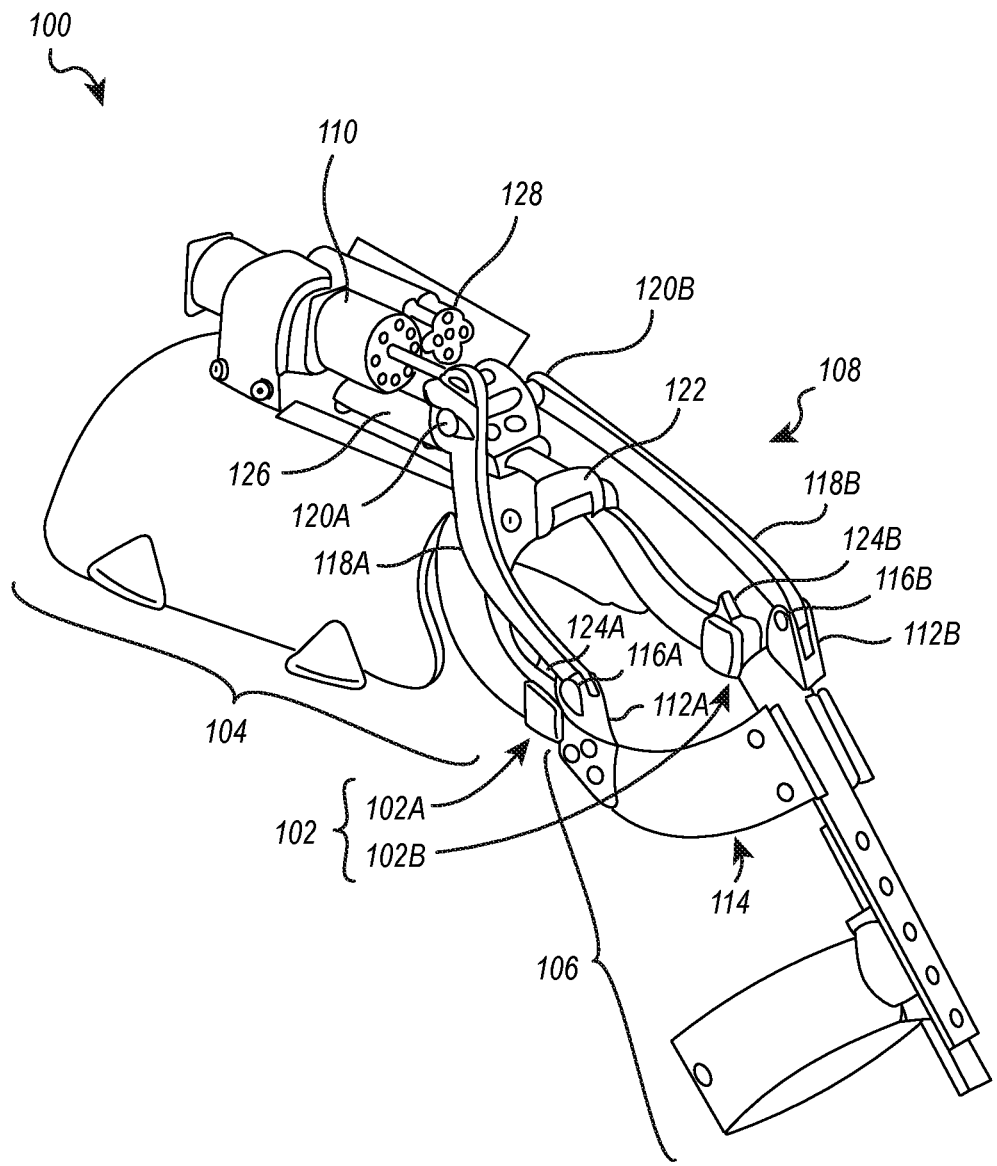
FIG. 1 illustrates a perspective view of example components of an exoskeleton device in a partially extended configuration.

Disclosed embodiments are directed to self-aligning mechanisms in passive and powered exoskeletons. Those skilled in the art will appreciate, in view of the present disclosure, that at least some of the embodiments disclosed herein may address various shortcomings associated with conventional exoskeletons.

For example, the self-aligning mechanisms of the present disclosure use a combination of prismatic and revolute passive degrees of freedom (pDOF) and/or elastic elements to dynamically align the anatomical and artificial joint. The self-aligning mechanisms are configured to transmit torque to the intended joint while reducing undesired loads on the limb. In some instances, the range of motion of the pDOFs of the self-aligning mechanisms of the present disclosure is substantially unaffected by differences in assistive torque applied or by misalignment between the artificial joint and the anatomical joint (e.g., indicating negligible friction in the pDOFs).

An exoskeleton device, as described herein, may be used to facilitate exoskeleton-assisted movement of a user limb. For example, a method for facilitating exoskeleton-assisted movement, in accordance with the present disclosure, may include various acts, such as arranging an exoskeleton device on a user limb, with an artificial joint of the exoskeleton device positioned about a joint of the user limb. A force may be applied by the exoskeleton device to first and second portions of the user limb (where the first and second portions of the user limb are on opposing longitudinal sides of the joint of the user limb). A self-aligning mechanism of the exoskeleton device, positioned about the first portion of the user limb, may advantageously compensate for misalignment between the artificial joint and the joint of the user limb. Such compensation contributes to reduced spurious forces and/or torques exerted on the first portion of the user limb by the exoskeleton device.

For instance, in one example implementation of a knee exoskeleton that includes a self-aligning mechanism in accordance with the present disclosure, peak spurious forces applied to the user's shank are below 10 N (e.g., about 5 N) and peak spurious torques applied to the user's shank are below 1 Nm (e.g., about 0.5 Nm) for an assistive torque of about 50 Nm applied by the knee exoskeleton (in a sit-to-stand experiment). By way of contrast, for a knee exoskeleton without a self-aligning mechanism, peak spurious forces and torques are typically within a range of about 50 N and 10 Nm, respectively.

The self-aligning mechanisms described herein allow for dynamic alignment of the actuated and anatomical axis for various types of user anatomies. This allows for exoskeletons with reduced need of customization and potentially less weight due to the decreased need for individual customization features. Furthermore, at least some exoskeletons of the present disclosure comprise a substantially symmetric artificial joint and/or frame structure, advantageously allowing the exoskeletons to be used on both right limbs and left limbs (e.g., on a user's right leg or a user's left leg) in the alternative without hardware modifications.

In addition, the self-aligning mechanisms of the present disclosure may be constructed in an advantageously lightweight manner so as to form only a small proportion of the total weight of the exoskeleton. For example, in some implementations, the self-aligning mechanism only accounts for less than about 6% (e.g., 5.3%, or 190 g) of the total weight of the exoskeleton (e.g., about 3.6 kg).

Having described some of the various high-level features and benefits of the disclosed embodiments, attention will now be directed to FIGS. 1 through 12. These Figures illustrate various supporting illustrations related to the disclosed embodiments.

Example Exoskeleton Devices

FIG. 1 illustrates a perspective view of example components of an exoskeleton device 100. The exoskeleton device 100 depicted in FIG. 1 is adapted for selectively applying power and/or torque to a user's knee joint (e.g., for assisting individuals with lower limb impairments). Although the exoskeleton device 100 of FIG. 1 may be regarded as a knee exoskeleton, the principles and techniques described herein may be applied to exoskeletons adapted for providing assistance to other bodily structures (e.g., waist, elbow, wrist, ankle, and/or other exoskeletons).

In the embodiment shown in FIG. 1, the exoskeleton device 100 includes an artificial joint 102 formed from a first component 102A and a second component 102B. The first component 102A is arranged on the exoskeleton device 100 for positioning on a first lateral side of a human joint (e.g., a human knee), whereas the second component 102B is arranged on the exoskeleton device 100 for positioning on a second, opposing lateral side of the human joint (see FIG. 2).

As is illustrated in FIG. 1, the artificial joint 102 of the exoskeleton device 100 comprises a rotation point between a thigh section 104 of the exoskeleton device 100 and a shank section 106 of the exoskeleton device 100. The artificial joint 102 may be formed, in some instances, using steel shafts and low friction plastic bushings, and/or other rotational mechanisms. The exoskeleton device 100 may apply an assistive torque to rotate the shank section 106 relative to the thigh section 104 about the artificial joint 102. In this way, when the exoskeleton device 100 is worn on a leg of a user, the assistive torque applies forces to the thigh and shank of the user's leg to provide assisted rotation of the user's knee about the user's knee joint.

To facilitate such functionality, the example exoskeleton device 100 depicted in FIG. 1 includes a slider-crank mechanism 108, which is connected to the artificial joint 102 and powered by a linear actuator 110. The slider-crank mechanism 108 of FIG. 1 includes separate slider-crank structures forming a four-bar mechanism. For example, as shown in FIG. 1, the separate slider-crank structures include a respective crank 112A, 112B connected to a frame member 114 that is also connected to the artificial joint components 102A and 102B. The respective cranks 112A and 112B connect via respective couplers 116A, 116B to respective sliders 118A, 118B, and the respective sliders 118A, 118B are connected at respective slider joints 120A and 120B. The respective slider joints 120A and 120B are configured to be driven by the linear actuator 110 and to travel along a rail 126 that extends along the thigh section 104 (e.g., along the top of a user's thigh).

The linear actuator 110 may take on any suitable form for actuating the slider joints 120A and 120B, such as a reaction force sensing elastic actuator (RFSEA). In some implementations, the actuator uses a ball screw system (e.g., 8×2 mm) where the nut is driven by a timing belt and supported by two angular contact bearings. The belt pulley system may, in some instances, have a 2.5:1 transmission ratio and be connected to a brushless DC motor. The actuator may feature a sliding element that acts as a bridge between the actuation system and the ground. This sliding element may anchor directly to the exoskeleton thigh frame and be connected to the actuation part through two pre-compressed coil springs. The ball screw may be supported by a low-friction linear guide that prevents radial loading on the ball screw.

The locations of the respective sliders 118A, 118B may impose a constraint on the offset of the four-bar mechanism (e.g., the distance between the artificial joints components 102A, 102B and the connection points of the cranks 112A, 112B to the frame member 114. The offset of the four-bar mechanism may be modified to tailor to the thigh dimensions of the expected user and/or class of users (e.g., 103 mm for a $50^{th}$ percentile male thigh).

FIG. 1 illustrates the exoskeleton device 100 in a partially extended configuration. The shank section 106 of the exoskeleton device 100 may be rotated relative to the thigh section 104 of the exoskeleton device about the artificial joint 102 to a full flexion position or a full extension position or to any position therebetween (e.g., by actuation of the linear actuator 110).

Furthermore, in some implementations, the exoskeleton device 100 includes a flexion end stop 122 integrated into the integrated into the thigh section 104 to limit the range of motion of the linear actuator 110 (e.g., resulting in a 100-degree maximum flexion knee angle, or other maximum flexion angle). Still furthermore, in some implementations, the exoskeleton device 100 includes extension end stops 124A, 124B integrated on frames of the thigh section 104 and the shank section 106 to prevent the artificial joint 102 (and any attached anatomical joint) from hyperextending.

FIG. 1 also illustrates that the exoskeleton device 100 can include electronics 128 (the functions and structure of which will be described hereinafter).

Figure 2:
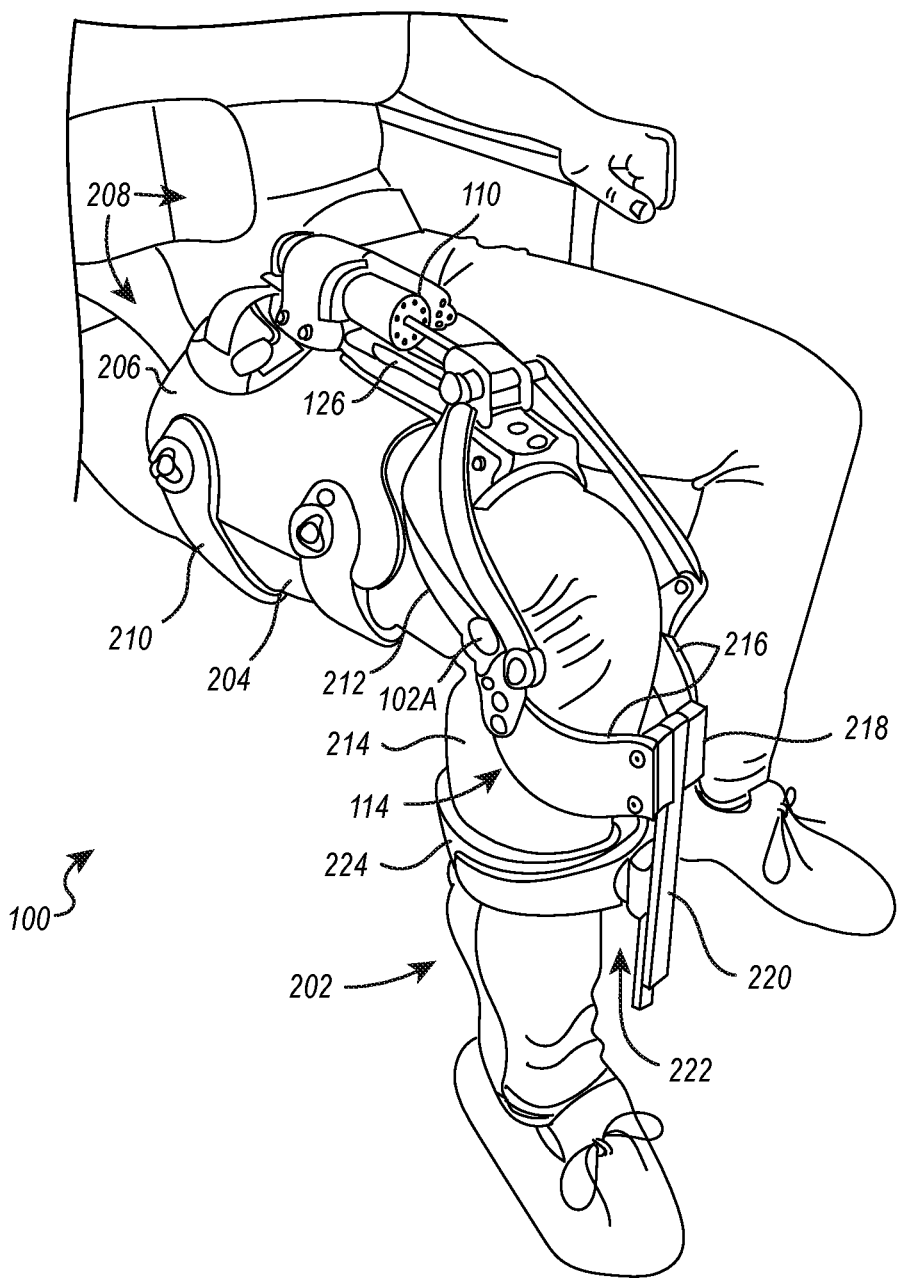
FIG. 2 illustrates a perspective view of an example exoskeleton device secured to a limb of a user in a flexed configuration.

FIG. 2 illustrates a perspective view of the exoskeleton device 100 secured to a limb of a user (in a partially flexed configuration). The limb of the user represented in FIG. 2 comprises the right leg 202 of the user. As is evident from FIG. 2, the linear actuator 110 is configured to be secured over the thigh 204 of the right leg 202 of the user.

For instance, FIG. 2 shows the linear actuator 110 affixed to a shell 206 of the exoskeleton device 100. The shell 206 may comprise a flexible plastic molded thigh shell, which may be flexible enough to allow users with different thigh sizes and/or shapes to use the exoskeleton device 100 in a comfortable manner. In some implementations, the inner surface of the shell 206 is lined with a hook and loop fastener (e.g., Velcro) or other fastening device, which allows the shell 206 to connect to a hip strap 208. The hip strap 208 of FIG. 2 can wrap around the user's waist and thigh (e.g., under the shell 206) and affix to the shell 206 to improve the physical connection between the exoskeleton device 100 and the user.

In some implementations, the shell 206 comprises one or more additional or alternative straps 210 to facilitate quick donning of the exoskeleton device 100. For example, the shell 206 may include straps 210 with a spin buckle system and/or magnetic buckles to facilitate quick affixation of the shell 206 to the thigh 204 of a user.

FIG. 2 also shows that the exoskeleton device 100 may be constructed from various frame members. For example, FIG. 2 illustrates a thigh frame 212 extending from a terminal portion of the rail 126 that guides the slider joints 120A and 120B. The thigh frame 212 extends toward the artificial joint component 102A. Although FIG. 2 only illustrates a single portion of the thigh frame 212 extending over the right portion of the user's right leg 202 toward the user's knee, the thigh frame 212 may include an opposite portion extending over the left portion of the user's right leg 202 (see FIG. 1).

FIG. 2 furthermore depicts the frame member 114 of the exoskeleton device 100. In particular, FIG. 2 shows the frame member 114 extending from the artificial joint 102 (or from the artificial joint components 102A and 102B) over the shank 214 of the right leg 202 of the user. In this regard, the artificial joint 102 may be regarded, in some instances, as an interface between the frame member 114 and the thigh frame 212.

In the example implementation depicted in FIG. 2, the frame member 114 includes a bridging element 216 that is connected to both of the artificial joint components 102A and 102B at different ends of the bridging element 216 (in addition to being connected to the respective cranks 112A and 112B). The bridging element 216 extends from the different artificial joint components 102A and 102B about the leg 202 of the user toward a central portion 218 of the bridging element 216 (e.g., in a C-shape). FIG. 2 furthermore illustrates a lower link 220 extending from the central portion 218 of the bridging element 216 so as to extend over and along the shank 214 of the right leg 202 of the user.

FIG. 2 illustrates a self-aligning mechanism 222 attached to the lower link 220. The self-aligning mechanism 222 includes a limb attachment member 224 that is configured for mechanically coupling to the shank 214 of the right leg 202 of the user, which is on the opposite longitudinal side of the knee joint of the right leg 202 relative to the thigh of the right leg 202 where the linear actuator affixes to the right leg 202.

Figure 3:
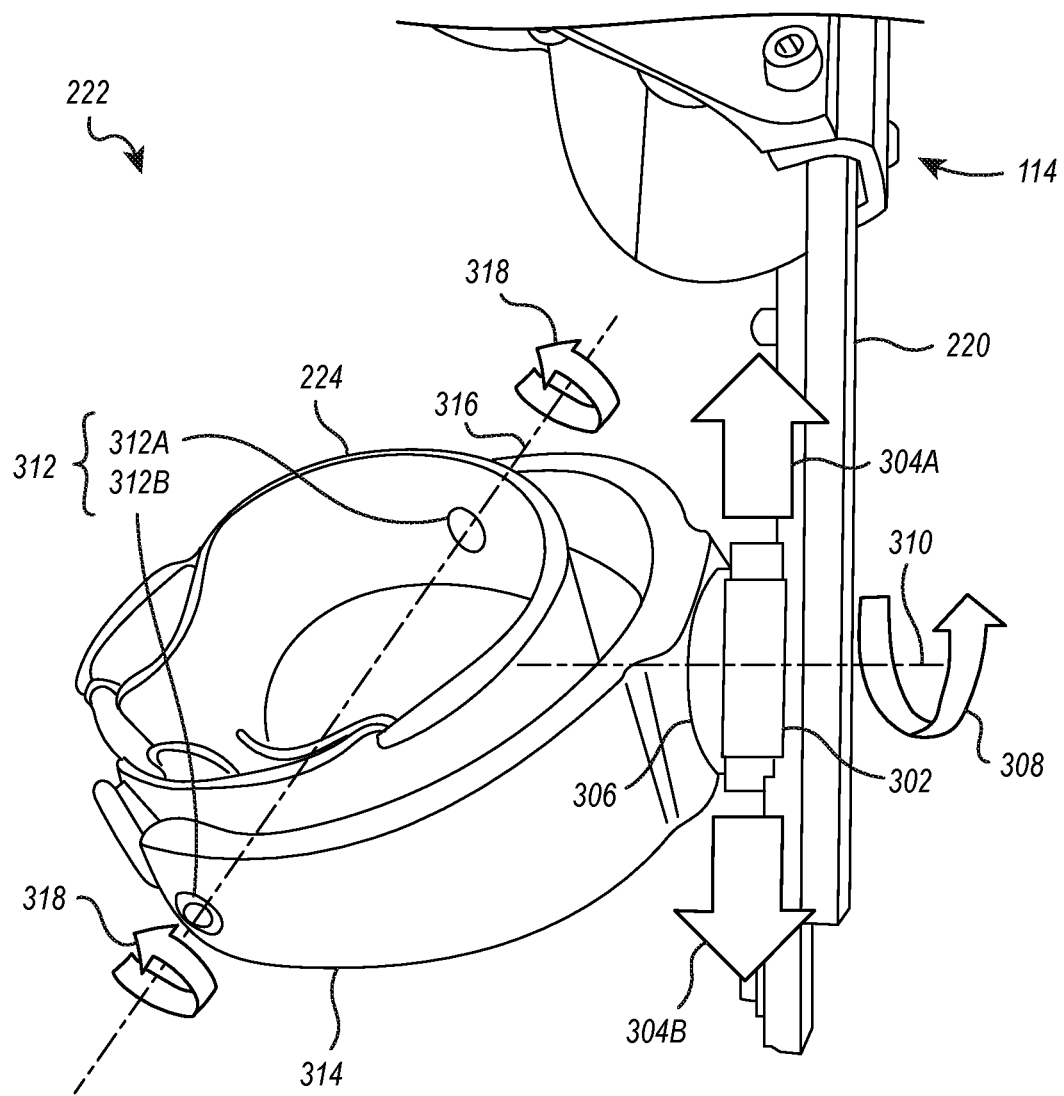
FIG. 3 illustrates a side view of an example self-aligning mechanism of an exoskeleton device.

Additional details of the self-aligning mechanism 222 will now be provided with reference to FIG. 3, which illustrates a side view of an example self-aligning mechanism 222 of the exoskeleton device 100. As noted above, the self-aligning mechanism 222 is connected to the lower link 220 extending from the bridging element 216 of the frame member 114.

FIG. 3 illustrates that, in some implementations, the self-aligning mechanism 222 includes three passive degrees of freedom (pDOF), which may be provided in a prismatic-revolute-revolute (PRR) configuration. The three pDOFs of the self-aligning mechanism 222 are, in some instances, integrated in series with the one active revolute DOF of knee flexion/extension facilitated by the artificial joint 102 as described above.

In one example, the prismatic pDOF of the self-aligning mechanism 222 is formed from a linear guide 302 connected to the lower link 220. The linear guide 302 may comprise a low-friction linear guide of various specifications (e.g., weight of about 150 g, about 750 mm range of motion (ROM), etc.) The directionality associated with the prismatic pDOF is illustrated in FIG. 3 by arrows 304A and 304B, indicating that the linear guide 302, as represented in FIG. 3, is able to slide along the lower link 220.

In the example illustrated in FIG. 3, the first revolute pDOF of the self-aligning mechanism 222 is formed by a rotary joint 306 that is connected to the linear guide (which is slidably connected to the lower link 220). The rotary joint 306 may be formed in any suitable manner, and may comprise, in some instances, a multi-turn joint with no mechanical stop (however, a mechanical stop may be implemented in some embodiments). The rotational direction associated with the first revolute pDOF is represented in FIG. 3 by arrow 308 and rotational axis 310, which indicates a rotation about a parasagittal plane of a user when the exoskeleton device 100 is worn on a leg of a user.

Furthermore, FIG. 3 shows that, in some instances, the second revolute pDOF of the self-aligning mechanism 222 is formed from a rotary element 312 (comprising a first component 312A and a second component 312B) that is connected to the rotary joint 306. For example, FIG. 3 illustrates a shank cuff 314 that connects to the rotary joint 306 at a central portion of the shank cuff 314. The shank cuff 314 also connects to the components 312A and 312B of the rotary element 312 on opposing ends of the shank cuff 314, with both components 312A and 312B of the rotary element 312 sharing a common rotational axis 316 (with rotation indicated by arrows 318). In this way, the rotary element 312, as shown in FIG. 3, is configured to revolve about a rotational axis 316 that is perpendicular to the rotational axis 310 associated with the rotary joint 306. For instance, while the rotational axis 310 of the rotary joint 306 lies on a parasagittal plane, the rotational axis 316 of the rotary element 312 lies on a frontal plane.

FIG. 3 illustrates the limb attachment member 224 of the self-aligning mechanism 222 affixed to the rotary element 312. In this way, the rotary element 312 may be regarded as connecting the limb attachment member 224 to the rotary joint 306. The limb attachment member 224 may be implemented as an adjustable strap, which allows adaptation to the different limb anatomies of different users.

In some implementations, the self-aligning mechanism 222 weighs less than 200 g (e.g., 190 g) or weighs less than 6% of the total weight of the exoskeleton device 100 (e.g., 5.3%). At least some aspects of the exoskeleton device 100 described herein contribute to significant benefits over existing exoskeleton systems.

Figures 4A, 4B, 4C:
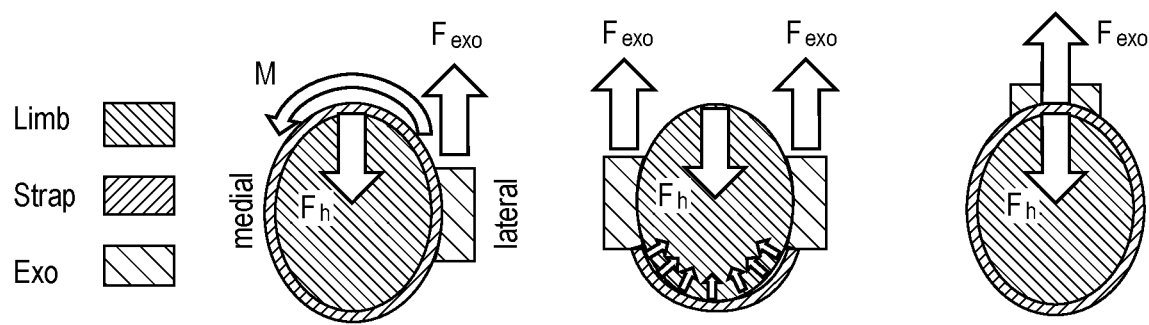
FIGS. 4A-4C illustrate schematic diagrams of different ways of attaching exoskeleton devices to user limbs.

For example, FIGS. 4A-4C illustrate schematic diagrams of different ways of attaching exoskeleton systems to user limbs (e.g., user legs). As depicted in FIGS. 4A-4C, $F_{exo}$ is the force applied by the exoskeleton and $F_h$ is the reaction force of the human limb. FIG. 4A illustrates a conventional exoskeleton system mounted to a user limb with assistive torque elements arranged lateral to the user limb, which causes a torsional moment M to be created by the $F_{exo}$ and $F_h$ couple.

In contrast with the approach shown in FIG. 4A, at least some implementations of the present disclosure use (i) the attachment configuration shown in FIG. 4B at the shank, where the force is transmitted to the limb through a soft flexible strap attached to the frame on both sides, and (ii) the attachment configuration shown in FIG. 4C at the thigh, where the force is transmitted through a soft flexible strap attached to a frame on the front of the limb. The configuration illustrated in FIG. 4B is facilitated at least in part by the placement of the first component 102A and the second component 102B of the artificial joint in parasagittal offset from the joint of the limb of the user, while the configuration illustrated om FIG. 4C is simultaneously facilitated at least in part by placement of the linear actuator 110 in parasagittal alignment with the joint of the limb of the user.

In this symmetric design configuration depicted in FIGS. 4B and 4C, the assistive exoskeleton force ($F_{exo}$) intersects the limb central axis. Thus, it generates no torsional moment (M), and thereby provides a key advantage over conventional exoskeleton systems. Thus, shear stress on the user's skin, which may cause discomfort and even pain, may be avoided. In addition, torsion on the exoskeleton frame at the point of contact with the user may be avoided by the design configuration depicted in FIGS. 4B and 4C. Thus, this configuration(s) disclosed herein can help the self-aligning mechanism 222 to avoid torsion (e.g., which could result in binding of the mechanism and, generally, may require heavier and bulkier structures and/or increased design complexity).

In some implementations, the symmetric design of the exoskeleton device 100 is facilitated by structuring each segment of the exoskeleton frame from two symmetrical halves for wrapping around the user's limb. The symmetric design can configure the exoskeleton device 100 for securement to a right leg of the user or to a left leg of the user without significant hardware modifications (e.g., the exoskeleton device 100 can be reversibly worn on a user's right leg or a user's left leg). The exoskeleton frame may be machined from any suitable material(s), such as 7075 aluminum alloy. These halves may be designed to fit any size range of users (e.g., a $50^{th}$ percentile male adult, resulting in 160 mm and 115 mm in diameter of the thigh and shank sections 104 and 106, respectfully), and/or may be selectively resizable (e.g., via the use of spacers).

Sensors and Embedded Electronics

Figure 5:
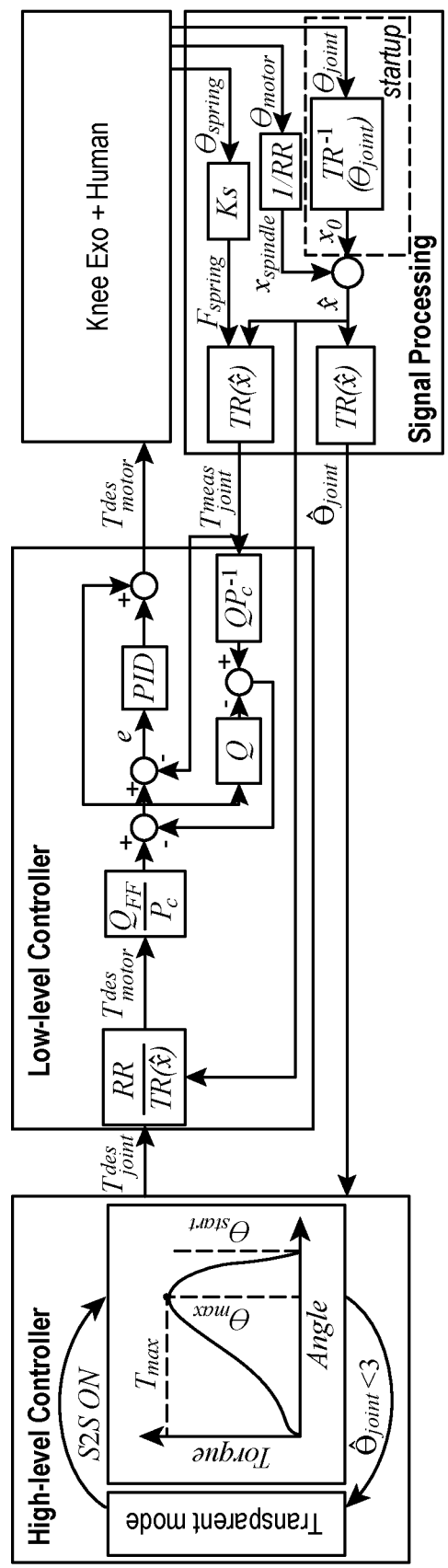
FIG. 5 illustrates a block diagram of control and signal processing systems associated with an exoskeleton device.
Figures 6A, 6B, 6C:
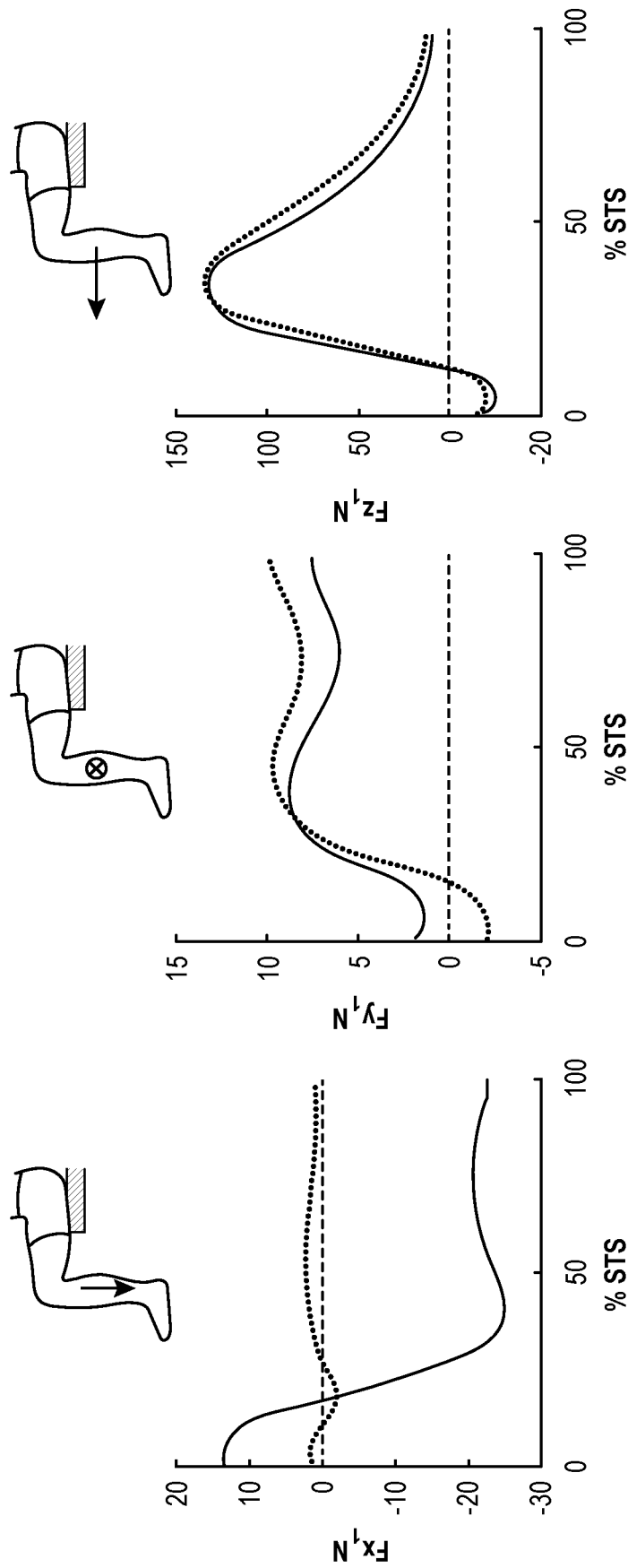
Figure 6F:
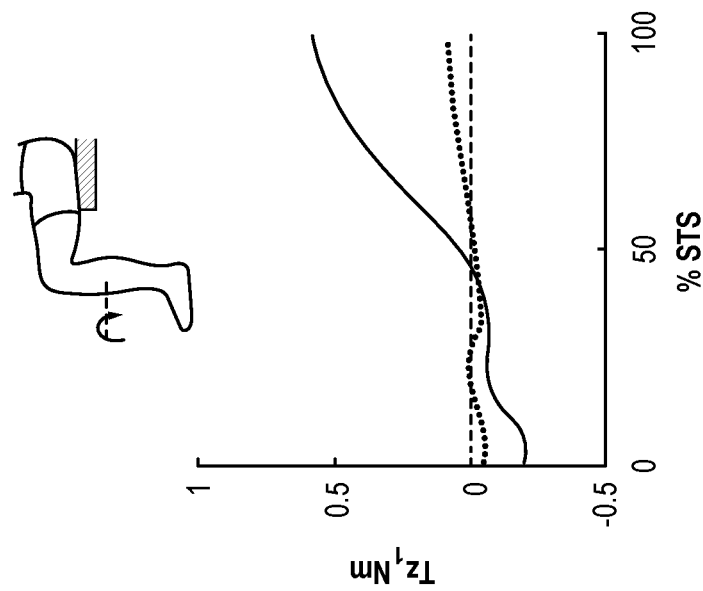
Figure 6E:
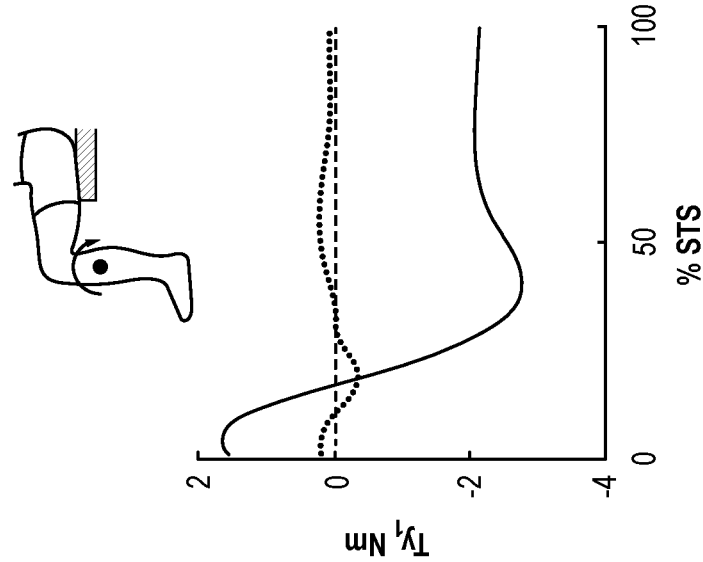
Figure 6D:
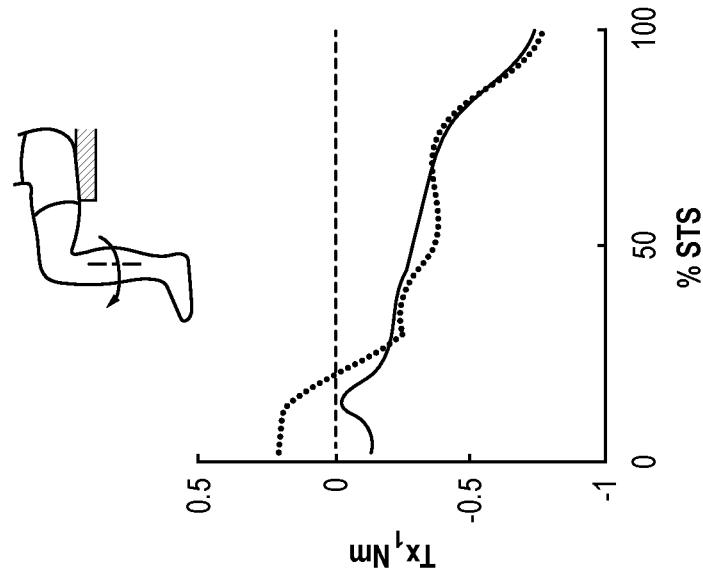

FIG. 5 illustrates an example block diagram of control and signal processing systems and/or techniques associated with an exoskeleton device 100. The exoskeleton devices of the present disclosure may comprise an array of sensors to accurately control the human-robot interaction (e.g., electronics 128). For instance, an exoskeleton device may include an absolute magnetic rotary encoder placed on the artificial/actuated joint of the exoskeleton for estimating the absolute knee joint position. An incremental magnetic rotary encoder located on the motor shaft may measure the position of the knee joint and may be used to estimate motor angular velocity. In addition, the linear actuator (e.g., RFSEA) may be equipped with a high-resolution rotary absolute encoder that measures the deflection of the linear springs using a capstan coupling. The capstan coupling converts the linear displacement due to the deflection of the springs into a proportional angular displacement of the encoder shaft, which may be driven by a cable (e.g., a steel cable).

For the purpose of testing, a 6-axis load cell may be integrated into the exoskeleton shank section to accurately measure the physical interaction between the user and the robot as necessary to assess the function of the self-aligning mechanism. The 6-axis load cell may use an off-the-shelf signal amplifier and a custom acquisition board. The force and torque recordings from the 6-axis load cell may be synchronized with the exoskeleton controller using a digital signal.

The exoskeleton device may be controlled, in some instances, using a custom embedded system including two different processing units that run the control routines and the secondary functions such as data logging and Wi-Fi communications. All time-critical routines such as sensor reading, filtering, joint position and torque control loops, may run at 2 kHz on a 32-bit microprocessor. The microprocessor may communicate with the motor current servo controller using PWM. The high-level control loops, data-logging, and user-communication may run on a single-board computer (e.g., at 500 Hz).

The single-board computer may communicate with the microprocessor using SPI. An external device may run a custom GUI for data monitoring and parameter-selection purposes and may communicate via using Wi-Fi with the single-board computer. The GUI may be used to change the control parameters and start/stop data saving. In addition, the control system may use a 1050 mAh 6-cell lithium-polymer battery, and/or a 5-V regulator to power the processing units, embedded sensors, and current servo controller. In some implementations, the electrical power consumption is 3.8 W and 3.1 W with Wi-Fi on and off, respectively. Furthermore, in some implementations, the weight of the embedded electrical system, including battery and protective covers, is 1.1 kg.

FIG. 5 illustrates an example control system that may be utilized in conjunction with the illustrated exoskeleton device or with other such exoskeleton devices integrating self-aligning mechanisms. At the high-level, a controller based on a finite-state machine defines the desired knee torque. At the low-level, a closed-loop torque controller with disturbance observer defines the desired motor current that is then imposed using a current driver. Raw signals are processed in the embedded electronics to estimate the angular position and torque at the knee joint.

A block diagram of the sensor processing is shown in FIG. 5. At startup, the absolute encoder ($\theta_{joint}$) estimates the absolute position of the slider ($x_0$) using the inverted four-bar kinematics ($TR_{(\theta_{joint})}^{-1}$. The absolute position of the slider is then used in combination with a relative slider position ($x_{spindle}$) estimated from the motor encoder ($\theta_{motor}$), to obtain an accurate (e.g., +/−0.011 mm) measurement of the slider position ($\hat{x}$). The slider position is used to calculate the position-dependent transmission ratio of the four-bar kinematics ($TR(\hat{x})$). Similarly, the knee joint torque ($T_{joint}^{meas}$) is estimated using the spring force ($F_{spring}$) combined with transmission ratio ($TR(\hat{x})$). The spring force ($F_{spring}$) is estimated by measuring the spring deflection ($\theta_{spring}$) in combination with the stiffness of the springs ($K_s$) and the transmission ratio ($TR(\hat{x})$).

At the low-level, a closed-loop controller is used to accurately track the desired knee-space torque ($T_{joint}^{des}$). First, the desired knee-space torque ($T_{joint}^{des}$) is transformed into an equivalent desired motor-space torque ($T_{motor}^{des}$) using the four-bar transmission ratio ($TR(\hat{x})$) and the combined timing-belt/ball screw transmission ratio (RR). The desired motor torque is then fed to a closed-loop proportional-integral-derivative (PID) regulator with disturbance observer (DOB). The RFSEA is modeled as a second-order system ($P_c$) as follows:

$$P_c(s) = \frac{800{,}000}{84.98s^2 + 4674s + 800{,}000}.$$

Exogenous forces and torques are handled as disturbances and fed as inputs to the system to compensate for the observed torques not resulting from the modeled system using feedforward ($Q_{FF}$) and feedback filters (Q). Finally, the desired motor torque ($T_{motor}^{des}$) is transmitted to the off-the-shelf current driver on the knee exoskeleton.

At the high-level, a torque-angle relationship based on healthy biomechanics defines the desired knee torque ($T_{joint}^{des}$) during sit-to-stand transitions solely as a function of the knee joint position ($\theta_{joint}$). As can be seen in FIG. 5, the desired knee torque starts at zero when the subject is seated, and the knee joint is flexed. As the user stands-up, the exoskeleton knee joint starts extending from its resting position. As a result, the desired exoskeleton torque increases from zero to a maximum value ($T_{max}$). From its maximum, the torque decreases with the knee joint position, finally reaching zero when the knee joint is fully extended. Notably, the user's knee angle at the start of the sit-to-stand transition depends on the user's anthropometry, chair height, and posture. To accommodate this variability, the knee angle at which the exoskeleton starts providing torque ($\theta_{start}$) equals the measured knee angle when the sit-to-stand controller is activated. Moreover, the desired peak torque ($T_{max}$) can be adjusted by the experimenter through a GUI. The knee angle at which the peak torque ($\theta_{max}$) is achieved, in some instances, at 30% between the starting and the ending angle. The torque-angle relationship may be implemented with a parametric Look-Up Table (LUT).

Example Results

FIGS. 6A-9 illustrate graphs of forces and torques applied to a portion of a user's limb by exoskeleton devices when using a self-aligning mechanism and when not using a self-aligning mechanism. In particular, the graphs represented by FIGS. 6A-9 were obtained according to an experimental protocol using an exoskeleton device 100 as described herein. The experimental protocol included two tasks: (i) standing up while assisted by the exoskeleton and (ii) tracking a desired position against a virtual impedance field generated by the powered exoskeleton. Both tasks were performed by subjects with the self-aligning mechanism in a "locked" configuration (with translation/rotation of the pDOFs of the self-aligning mechanism restricted) and with the self-aligning mechanism in an "unlocked" configuration (with translation/rotation of the pDOFs unrestricted).

The results show that the self-aligning mechanism (e.g., self-aligning mechanism 222, as discussed above) significantly reduces the spurious forces and torques on the user for both tasks. The results of the experimental protocol also demonstrated an increased level of user comfort facilitated by the reduction in spurious forces and torques. These results demonstrate the efficacy of self-aligning mechanisms in improving comfort and performance during sit-to-stand and position tracking tasks with a powered knee exoskeleton.

The mass of the self-aligning mechanism, which is not considered in theoretical models, has a critical, negative effect on its function. For example, gravity can cause the prismatic pDOF of a self-aligning mechanism to slide and reach its mechanical end-stop, effectively impairing the self-aligning function. Similarly, inertial forces and torques due to the mass of the self-aligning mechanism can cause its passive joints to move during activity. These unmodeled and uncontrolled movements are likely to limit the potential reduction of spurious forces and torques and can cause discomfort to the user. Thus, utilizing a relatively small mass for a self-aligning mechanism as described herein (e.g., about 190 g, about 5.3% of the overall exoskeleton mass, etc.) contributes to the observed improvements in comfort and performance.

Reducing the mass of a self-aligning mechanism without impairing its function under load is associated with many challenges, in particular because the passive joints of a self-aligning mechanism must be able to move freely while transferring the assistive torque. For example, the prismatic joint/pDOF must be able to slide freely while transferring the force $F_z$ (see FIG. 6C) so that the powered exoskeleton can provide assistive or resistive torques at the user's knee joint. In some implementations, a relatively large linear guide 302 is used (150 g, 3.5 kN max load). Although a smaller and lighter linear guide would reduce the overall mass, it may increase friction, which could impair the movement of the passive joints under load.

Notably, the symmetric design of the powered exoskeleton as discussed above has a beneficial effect on the function of the self-aligning mechanism. The symmetric design minimizes the torque on the linear guide, allowing for both the mass and the friction of the self-aligning mechanism to be minimized. Similarly, the symmetric design reduces the load that the linkages of the self-aligning mechanism must withstand. This load reduction is beneficial because deformations in the linkages of the self-aligning mechanism may impair the ability of its passive joints to move freely under load.

The comfort and effort during each experimental condition were assessed using questionnaires filled out by the subjects at the end of each test (i.e., standing-up and tracking tasks, with the exoskeleton device in locked and unlocked configurations). The results show that the presence of the self-aligning mechanism significantly improves comfort during both the standing-up and the tracking task. Interestingly, the tracking task was reported to be significantly more comfortable than the standing-up task. This result may be explained by the fact that the spurious forces and torques were greater during the standing-up task than the tracking tasks. Thus, these results suggest that there is a correlation between the spurious forces and torques and the user's comfort. The results suggest that these interaction forces and torques were large enough for the subjects to feel less comfortable using the locked configuration than when using the unlocked configuration.

Performance during the standing-up task was assessed using the root-mean-square error between the center of pressure (CoP) and the midline of a force plate on the self-aligning mechanism and the maximum deviation of the CoP from the midline. The results show that both performance metrics were significantly better (up to 32%) in the presence of the self-aligning mechanism (i.e., under the unlocked configuration). Performance during the tracking task was assessed using the RMS error between the target wave and measured knee angle. The RMS error was significantly lower in the unlocked configuration than the locked configuration (38%).

Figure 7:
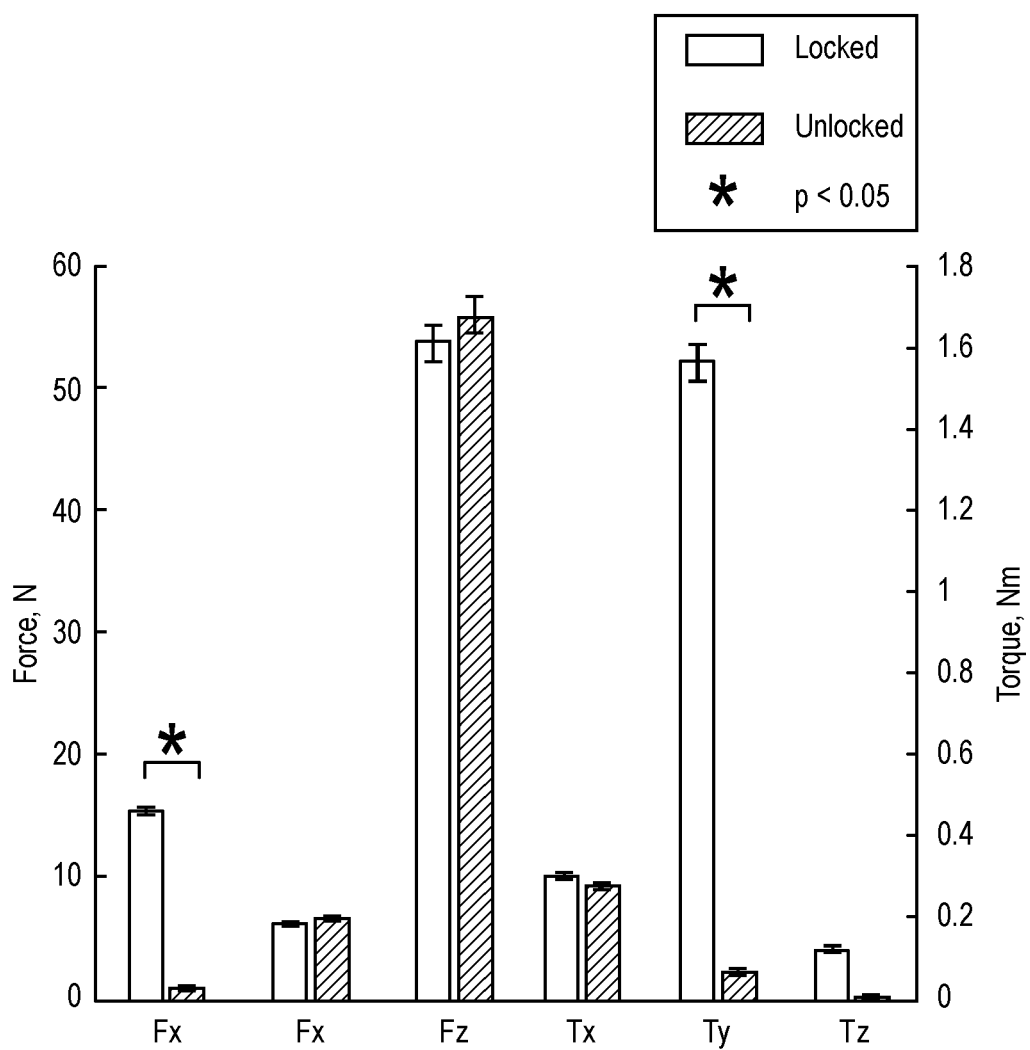
Figure 9:
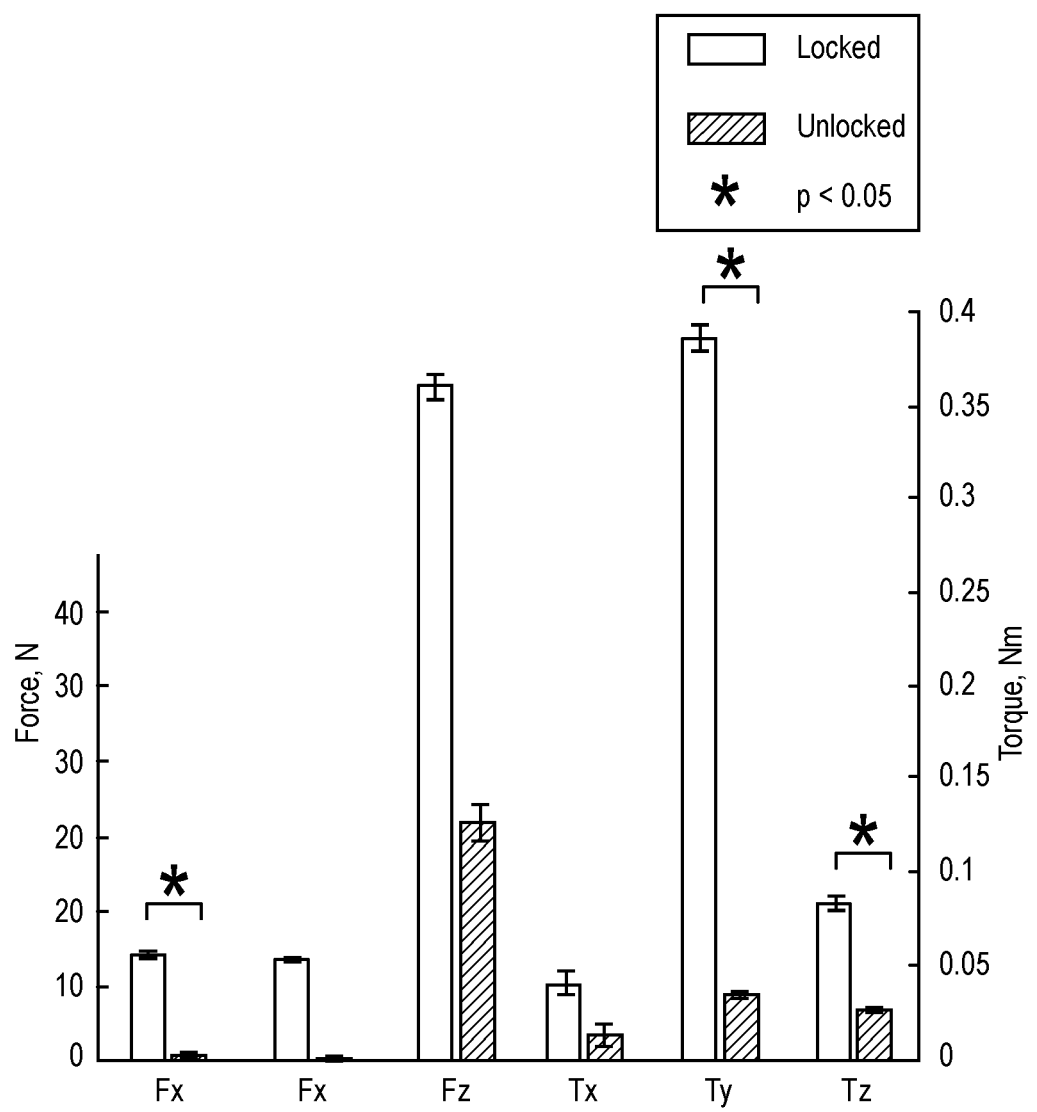

FIGS. 6A-6F illustrate the mean values of the interaction forces and torques between the subjects' shank and the exoskeleton device during the sit-to-stand (STS) task with the exoskeleton device under locked and unlocked configurations. FIG. 7 provides a bar plot of absolute values of average forces and torques for the STS task for both the locked and unlocked configurations, with error bars showing standard error. Similarly, FIGS. 8A-8F illustrate the mean values of the interaction forces and torques between the subjects' shank and the exoskeleton device during the tracking (TRK) task with the exoskeleton device under locked and unlocked configurations. FIG. 9 provides a bar plot of absolute values of average forces and torques for the TRL task for both the locked and unlocked configurations, with error bars showing standard error.

As is evident from FIGS. 6A-9, the averages of $F_y$ and $F_z$ are similar for the locked and unlocked configurations during the standing-up task but not for the tracking task. Furthermore, FIGS. 6A-9 show that, during the tracking task, $F_y$ and $F_z$ appear to follow similar trajectories, however, under the unlocked configuration, the data is offset compared to the locked configuration. This variation in $F_y$ and $F_z$ between conditions may have been caused by the position of the loadcell with respect to the active joint of the powered exoskeleton, which may change when the self-aligning mechanism is in the unlocked condition because the loadcell can slide along the frame of the exoskeleton. Interestingly, during the standing-up task, the average value of $F_z$ is slightly higher in the unlocked configuration than in the locked configuration. With the unlocked configuration, only $F_z$ contributes to generating the desired flexion/extension torque on the user's knee. In contrast, with the locked configuration, both $F_z$ and $T_y$ contribute to transfer the knee flexion/extension torque to the user's knee, indicating a potential for a purer translation of torque between the exoskeleton and the human limb during the unlocked configuration.

The results shown in FIGS. 6A-9 show that the presence of the self-aligning mechanism (i.e., the unlocked configuration) can lead to a significant decrease in the average values for $F_x$, $T_y$, and $T_z$ during both standing-up and tracking tasks. This reduction is facilitated at least in part by the self-aligning mechanism implemented in the exoskeleton device that comprises three pDOFs, allowing translational movements along a first axis and rotational movements around the two additional axes that are perpendicular to one another. These result shows that the proposed self-aligning mechanism has a significant effect on spurious forces and torques. For different specific kinematics or mechanical implementations, a self-aligning mechanism can be used to achieve similar comfort and performance improvement, provided it can show a similar reduction in spurious forces and torques.

Additional Embodiments

Figure 10:
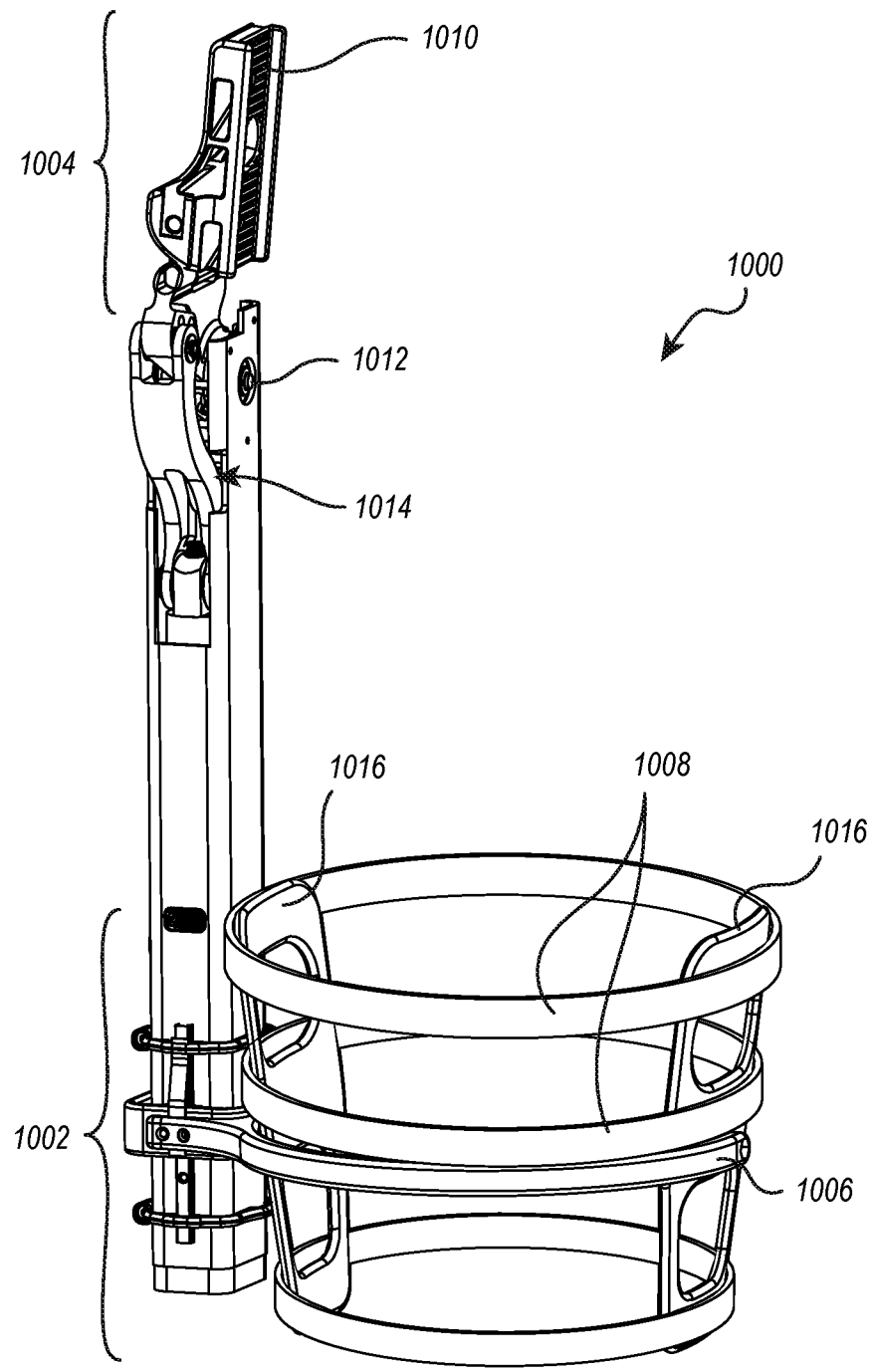
FIG. 10 illustrates a perspective view of example components of a hip exoskeleton, in accordance with the present disclosure.

As indicated hereinabove, a self-aligning mechanism may be implemented on various types of exoskeleton devices and are not limited to knee exoskeletons. For example, FIG. 10 illustrates a hip exoskeleton 1000, which includes a lower interface 1002 for connecting to a thigh of a user as well as an upper interface 1004 for connecting to a hip of a user. The lower interface 1002 includes a thigh cuff 1006 (e.g., formed from rigid plastic and nylon straps) as well as elastic elements 1008 (e.g., thick surgical rubber) for securing to a thigh of a user (e.g., forming a thigh orthosis). The thigh orthosis distributes resultant forces across a large portion of the distal thigh and may include load distributing bars 1016.

The upper interface 1004 includes an attachment member 1010 that is configured to connect to a pelvis pad (not shown) that wraps around the user's hips (e.g., forming a pelvis orthosis). A pelvis orthosis may include separate elements for attachment to opposing sides of the pelvis of a user. The separate elements may be connected by straps (e.g., spin buckle straps). The pelvis orthosis may include an anti torsion bar that resists independent movement of the pelvis orthosis and transfers sagittal plane moments to the sacral and lumbar portions of the lower back. The anti-torsion bar may also store the electronics and/or battery for the hip exoskeleton 1000.

The hip exoskeleton 1000 includes an artificial joint 1012 configured for positioning about the hip of the user to provide an active DOF for facilitating the application of assistive torque to the hip of the user.

The hip exoskeleton 1000 of FIG. 10 utilizes an offset slider-crank mechanism 1014 to facilitate assistive torque. In some implementations, the offset slider-crank mechanism 1014 may be powered by a linear actuator (e.g., including a brushless DC motor and a primary helical gear transmission) coupled with a high-efficiency ball screw. A linear guide may support the perpendicular load on the ball screw nut. Angular contact ball bearings may support radial and axial loads on the helical gears, and translation of the screw nut and linear guide block along the rail may be converted to rotation of the actuated artificial joint 1012 through composite compliant bars, creating a series elastic actuator. Lightweight, low-friction dry bushings may support the load of the actuated artificial joint 1012.

Figure 11:
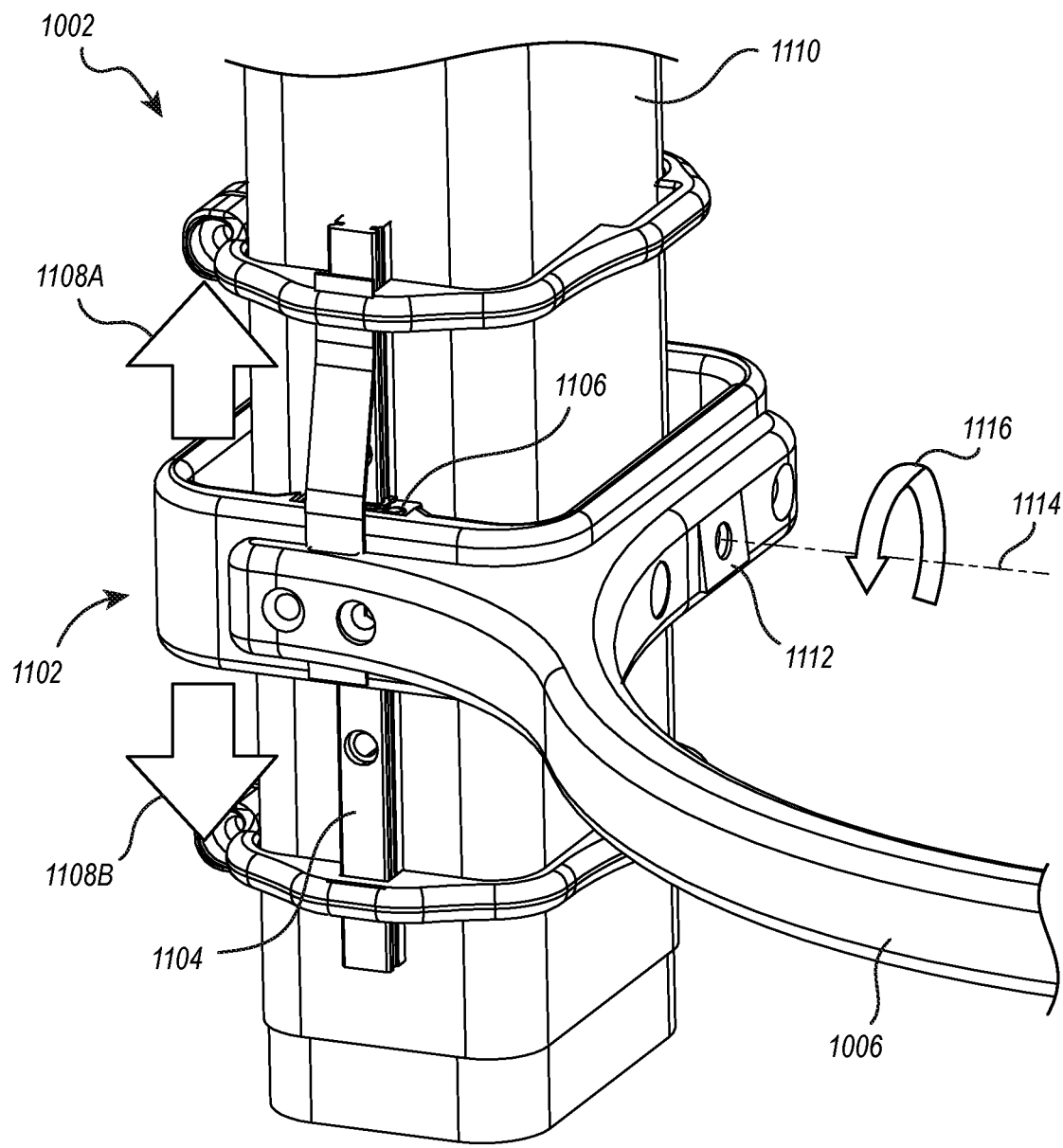
FIG. 11 illustrates a close-up perspective view of a lower interface of a hip exoskeleton.

FIG. 11 illustrates a close-up view of the lower interface 1002 of the hip exoskeleton 1000. As is illustrated in FIG. 11, the lower interface 1002 includes a self-alignment mechanism 1102 to facilitate a reduction in spurious forces and torques that become applied to the user's hip. In particular, the self-alignment mechanism 1102 comprises one or more rails 1104 with one or more linear guides 1106 attached thereto (e.g., with corresponding rails and linear guides on multiple sides of the shaft 1110 of the hip exoskeleton 1000), providing a prismatic pDOF (with directionality indicated by arrows 1108A and 1108B).

The self-alignment mechanism 1102 also includes a revolute pDOF provided by a rotary joint 1112 coupled to the one or more linear guides 1106 and connected to the thigh cuff 1006 to facilitate passive rotation of the thigh cuff 1006 about an axis that is perpendicular to the translational axis associated with the prismatic pDOF (indicated in FIG. 11 by axis 1114 and arrow 1116). The self-alignment mechanism 1102 contributes to a reduction in the spurious forces and torques applied by the hip exoskeleton 1000 to the user's body.

Figure 12:
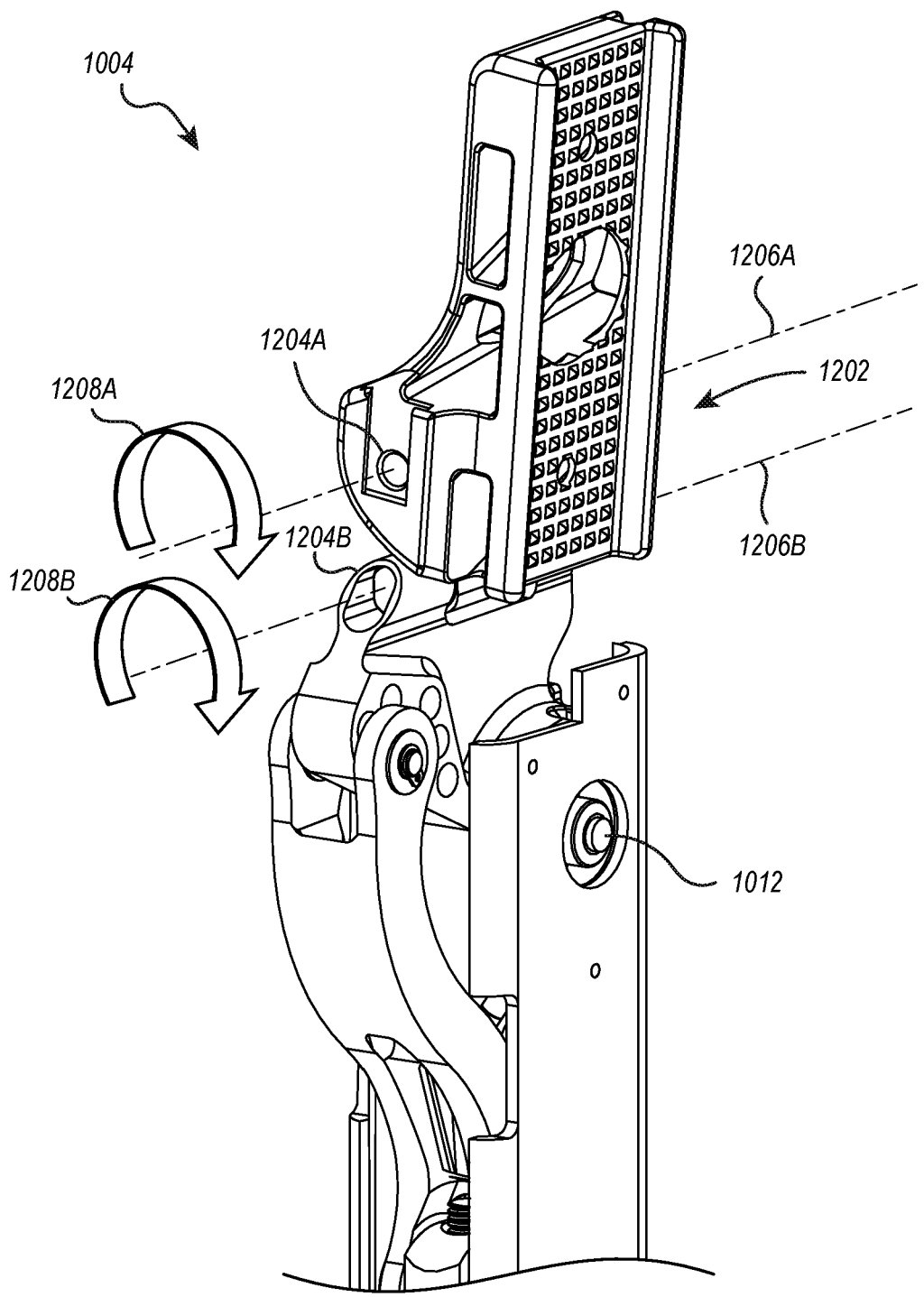
FIG. 12 illustrates a close-up perspective view of an upper interface of a hip exoskeleton.

FIG. 12 illustrates a close-up view of the upper interface 1004 of the hip exoskeleton 1000. In particular, FIG. 12 illustrates that the upper interface 1004 may comprise a separate self-alignment mechanism 1202 that includes a pair of revolute pDOFs formed by separate rotary joints 1204A and 1204B and that are configured in series with the active DOF of the artificial joint 1012. The pDOFs of the self-aligning mechanism 1202 may allow for unconstrained hip abduction and/or adduction. The pair of revolute pDOFs rotate about parallel rotational axes 1206A and 1206B (indicated by arrows 1208A and 1208B). The self-alignment mechanism 1202 contributes to a reduction in the spurious forces and torques arising from any misalignment between the powered flexion/extension axis of the hip exoskeleton 1000 and the user's anatomical flexion/extension axis, particularly in combination with the self-alignment mechanism 1102.

The following provides an overview of example sensing and power electronics that may be implemented with a hip exoskeleton 1000. The hip exoskeleton 1000 may include a power supply, such as a 1200 mAh, six-cell lithium-ion (LiIon) battery. A 5-V regulator may be implemented to scale the supply voltage as needed to power the embedded computer and analog sensors. A 3.3-V regulator may power the microcontroller and operate as the logic voltage for the digital sensors. Two separate processing units may be implemented in the motherboard to run the control routines and secondary functions, such as data saving and Wi-Fi communications. All time-critical routines, such as sensor reading, filtering, joint position, torque control loops, etc., may run at 1 KHz on a microcontroller (e.g., a 32-bit microcontroller). The microcontroller may use pulse-width modulation (PWM) to communicate to the two motor servo drives, which run the closed-loop motor current control at 50 kHz.

The microcontroller may use dedicated serial peripheral interface (SPI) busses to communicate with the embedded sensors and an embedded, single-board computer, which may run the high-level control loops, data saving, and user communication (e.g., at 500 Hz). The embedded single-board computer may communicate with a remote device using Wi-Fi. The remote device may run a custom graphical user interface (GUI) for data monitoring and parameter-selection purposes. Using the GUI, a user can modify the high-level control parameters while the device is operating. The operating system for the embedded computer may be stored on a single SD card, which may also be used for data storage. The microprocessor, the embedded single-board computer, the motor servo drives, and the voltage regulators may be integrated on a custom motherboard. The electrical system, including the power supply, may be fully enclosed in a custom protection cover, which may connect to the back of the pelvis interface. In some implementations, the electrical power consumption is 3.6 W and 3.1 W, respectively, with Wi-Fi on and off.

Sensor circuit boards may be housed within the hip exoskeleton frame. A 14-bit magnetic absolute encoder board may measure the hip flexion/extension angle and be located at the proximal end of the carbon fiber frame. An inertial measurement unit (IMU) board may measure the accelerations and rotational speeds and be located at the distal end of the carbon fiber frame. Both custom circuit boards may communicate with the microcontroller using SPI. A dedicated, shielded wire may be used to transmit the digital data from the sensors to the motherboard. An incremental encoder may be used to measure the position of the motor shaft for torque control purposes. Hall sensors embedded in the motor may be used for commutation by the servo drives. The signal from the incremental encoder and hall sensors may be transmitted to the motherboard using a dedicated shielded wire. Another cable carrying the motor power stage current may connect the exoskeleton to the motherboard.

A hierarchical controller may provide synchronous assistance during ambulation. At the high-level, an adaptive frequency oscillator (AdOsc) may estimate the gait cadence of the coupled human-exoskeleton system. Estimation of the cadence may be combined with information about the start of the gait cycle to provide a continuous estimate of the gait cycle evolution (e.g., 0-100% stride completion). The peak of the hip extension angle may be used as the start of the gait cycle.

A finite-state machine may detect the peak of the hip flexion angle, indicating the start of the gait cycle. The finite state machine may include two states: peak flexion and swing preparation/initiation, and the state machine may take as input the angular orientation and velocity of the thigh in the sagittal plane. These input variables may be estimated by a complementary filter combining the accelerometer and gyroscope data from the IMU. A low-pass filter may be applied to the thigh orientation to reduce noise and increase robustness. Notably, the delay introduced by the filter may be accounted for when tuning the timing of the assistance. When the thigh orientation is higher than a predefined threshold (e.g., the hip joint is flexed) and the thigh velocity is lower than a predefined negative threshold (e.g., the thigh is extending), the finite-state machine may transition between peak flexion state and swing preparation/initiation state. This transition may indicate that a suitable peak of hip flexion has been detected, triggering the start of the gait cycle. From swing preparation/initiation state, the finite state machine may transition back to peak flexion state when the thigh orientation is lower than a predefined threshold (i.e., the hip joint is extended).

The powered hip exoskeleton 1000 can be used in bilateral or unilateral configuration, and the two actuation modules may be interchangeable. Each actuation module may have a dedicated finite-state machine and adaptive oscillator. When the exoskeleton is used bilaterally, the user may have the option to use dedicated finite-state machines and adaptive oscillators for each actuation module. In this case, the modules are controlled independently of one another, using their own percent stride estimate to generate assistance. Alternatively, the user may have the option to select the finite-state machine and adaptive oscillator of one actuation module to control both actuation modules. If the user chooses to use the finite-state machine and adaptive oscillator from only one actuation module, then the desired torque of the contralateral side may be delayed by 50% of stride. The latter option can be used, for example, with hemiparetic subjects to use the unaffected side to control the movement of the affected side.

The middle-level controller defines the desired assistive torque based on the gait phase estimate (e.g., percent stride) received from the high-level controller. The desired assistive torque is defined using two Gaussian functions—one for flexion and one for extension. Each Gaussian function may include three parameters that can be adjusted by the user through the graphical user interface:

$$T(t) = T_{flx} e^{-\frac{(x-t_{flx})^2}{2w_{flx}^2}} - T_{ext} e^{-\frac{(x-t_{ext})^2}{2w_{ext}^2}}$$

The first parameter is the peak of the torque (i.e., $T_{flx}$, $T_{ext}$). The second parameter is the timing, or percent stride, at which the peak of the torque happens (i.e., $t_{flx}$, $t_{ext}$) of the peak of torque. The third parameter is the duration of the assistance, which is adjusted by changing the width of the Gaussian functions (i.e., $w_{flx}$, $w_{ext}$). The desired torque obtained by the gaussian function may then be scaled by the user's body mass. The user has the option to use different parameters for the left and right sides of the powered hip exoskeleton or to use the same parameters.

The low-level controller converts the desired assistive torque into a desired motor torque for the servo motor. The torque controller may include a feedforward command based on the position-dependent transmission ratio. This feedforward command may include a constant factor ($\eta$) that compensates for the efficiency of the actuation system. In addition, two compensators may be implemented to modify the dynamic effects of the transmission system on the output torque increasing fidelity and reducing the apparent impedance at the output joint. Both compensators may take as input the motor position measured by the incremental encoder. The first compensator may generate an online estimate of the viscous torque due to the linear actuator velocity. The second compensator may compute a scaled and low-pass-filtered estimate of the transmission inertia. The desired current may be calculated by first adding the feedforward term to the compensators estimates and then dividing by the torque constant of the motor.

Although walking, running, and stairs climbing are periodic activities, the kinematic profiles are different. The periodicity of each activity may allow the AdOsc to learn the frequency of each task, and the state machine parameters may be further tuned to fit the kinematics. Furthermore, the peak assistance and timing are different for walking, running, and stairs. However, the high-level control algorithm is, in some instances, fundamentally unchanged between user activity. Therefore, a series of parameters may be tuned for each of the tasks such that a desired assistance profile could be reliably generated.

Additional Exemplary Aspects

Embodiments of the present disclosure may include, but are not necessarily limited to, features recited in the following clauses:

Clause 1: An exoskeleton device, comprising: an artificial joint; a frame member extending from the artificial joint configured for extension over a limb of a user; and a self-aligning mechanism connected to the frame member, the self-aligning mechanism comprising three passive degrees of freedom (pDOF) provided in a prismatic-revolute-revolute (PRR) configuration, the self-aligning mechanism comprising a limb attachment member configured for mechanically coupling to a portion of the limb of the user.

Clause 2: The exoskeleton device of Clause 1, wherein the artificial joint comprises a first component and a second component, the first component and the second component being configured for positioning on opposing lateral sides of a joint of the limb of the user.

Clause 3: The exoskeleton device of Clause 2, wherein the frame member comprises a bridging element, the bridging element being connected to both the first component and the second component on opposing ends of the bridging element, and wherein the frame member includes a lower link extending from a central portion of the bridging element, the lower link being configured to extend along the limb of the user.

Clause 4: The exoskeleton device of Clause 3, wherein a prismatic pDOF of the self-aligning mechanism is formed from a linear guide connected to the lower link.

Clause 5: The exoskeleton device of Clause 4, wherein a first revolute pDOF of the self-aligning mechanism is formed by a rotary joint connected to the linear guide slidably connected to the lower link.

Clause 6: The exoskeleton device of Clause 5, wherein a second revolute pDOF of the self-aligning mechanism is formed by a rotary element connected to the rotary joint, the rotary element being configured to revolve about a second rotational axis that is perpendicular to a first rotational axis associated with the rotary joint.

Clause 7: The exoskeleton device of Clause 6, wherein the limb attachment member is connected to the rotary element.

Clause 8: The exoskeleton device of any one of Clauses 1-7, wherein the self-aligning mechanism weighs less than 200 g.

Clause 9: The exoskeleton device of any one of Clauses 1-8, wherein the self-aligning mechanism forms less than 6% of a total weight of the exoskeleton device.

Clause 10: The exoskeleton device of any one of Clauses 1-9, wherein the artificial joint is connected to a slider-crank mechanism, the slider-crank mechanism being powered by a linear actuator.

Clause 11: The exoskeleton device of Clause 10, wherein the artificial joint comprises a first component and a second component configured for positioning on opposing lateral sides of a joint of the limb of the user, and wherein the slider-crank mechanism comprises a four-bar mechanism, the four-bar mechanism comprising: a first slider-crank structure connected between the linear actuator and the first component of the artificial joint; and a second slider-crank structure connected between the linear actuator and the second component of the artificial joint.

Clause 12: The exoskeleton device of Clause 11, wherein the linear actuator is configured for securement over a second portion of the limb of the user, the second portion being on an opposing longitudinal side of the joint of the limb relative to the portion of the limb of the user.

Clause 13: The exoskeleton device of Clause 12, further comprising a shell connected to the linear actuator, the shell being configured to form about the second portion of the limb of the user.

Clause 14: The exoskeleton device of Clause 13, further comprising a strap connected to the shell and configured to secure the shell to the second portion of the limb of the user.

Clause 15: The exoskeleton device of any one of Clauses 12-14, wherein the linear actuator is configured for securement over the second portion of the limb in parasagittal alignment with the joint of the limb of the user.

Clause 16: The exoskeleton device of Clause 15, wherein the first component and the second component of the artificial joint are configured for positioning in parasagittal offset from the joint of the limb of the user.

Clause 17: The exoskeleton device of any one of Clauses 12-16, wherein the limb is a leg of the user, and wherein the portion of the limb is a shank of the leg, and wherein the second portion of the limb is a thigh of the leg, and wherein the joint of the user is a knee of the leg.

Clause 18: The exoskeleton device of Clause 17, wherein the exoskeleton device is configured for securement to a right leg of the user, and wherein the exoskeleton device is configured for securement to a left leg of the user.

Clause 19: A method for facilitating exoskeleton-assisted movement, comprising: arranging an exoskeleton device on a user limb with an artificial joint of the exoskeleton device positioned about a joint of the user limb; applying a force to a first portion and a second portion of the user limb with the exoskeleton device, the first portion and the second portion of the user limb being on opposing longitudinal sides of the joint of the user limb; and compensating for misalignment between the artificial joint and the joint of the user limb with a self-aligning mechanism of the exoskeleton device, the self-aligning mechanism being positioned about the first portion of the user limb, the self-aligning mechanism comprising three passive degrees of freedom (pDOF) provided in a prismatic-revolute-revolute (PRR) configuration, wherein the compensation contributes to reduced spurious forces and/or torques exerted on the first portion of the user limb by the exoskeleton device.

Clause 20: The method of Clause 19, wherein, for an assistive torque of about 50 Nm applied on the user limb by the exoskeleton device, a peak spurious force exerted on the first portion of the user limb by the exoskeleton device is below 10 N and a peak spurious torque exerted on the first portion of the user limb by the exoskeleton device is below 1 Nm.

CONCLUSION

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. An exoskeleton device, comprising:
an artificial joint;
a frame member extending from the artificial joint configured for extension over a limb of a user; and
a self-aligning mechanism connected to the frame member, the self-aligning mechanism comprising three passive degrees of freedom (pDOF) provided in a prismatic-revolute-revolute (PRR) configuration, the self-aligning mechanism comprising a limb attachment member configured for mechanically coupling to a portion of the limb of the user,
wherein the artificial joint is connected to a slider-crank mechanism, the slider-crank mechanism being powered by a linear actuator, and
wherein the artificial joint comprises a first component and a second component configured for positioning on opposing lateral sides of a joint of the limb of the user, and wherein the slider-crank mechanism comprises a four-bar mechanism, the four-bar mechanism comprising:
a first slider-crank structure connected between the linear actuator and the first component of the artificial joint; and
a second slider-crank structure connected between the linear actuator and the second component of the artificial joint.

2. The exoskeleton device of claim 1, wherein the frame member comprises a bridging element, the bridging element being connected to both the first component and the second component on opposing ends of the bridging element, and wherein the frame member includes a lower link extending from a central portion of the bridging element, the lower link being configured to extend along the limb of the user.

3. The exoskeleton device of claim 2, wherein a prismatic pDOF of the self-aligning mechanism is formed from a linear guide connected to the lower link.

4. The exoskeleton device of claim 3, wherein a first revolute pDOF of the self-aligning mechanism is formed by a rotary joint connected to the linear guide slidably connected to the lower link.

5. The exoskeleton device of claim 4, wherein a second revolute pDOF of the self-aligning mechanism is formed by a rotary element connected to the rotary joint, the rotary element being configured to revolve about a second rotational axis that is perpendicular to a first rotational axis associated with the rotary joint.

6. The exoskeleton device of claim 5, wherein the limb attachment member is connected to the rotary element.

7. The exoskeleton device of claim 1, wherein the self-aligning mechanism weighs less than 200 g.

8. The exoskeleton device of claim 1, wherein the self-aligning mechanism forms less than 6% of a total weight of the exoskeleton device.

9. The exoskeleton device of claim 1, wherein the linear actuator is configured for securement over a second portion of the limb of the user, the second portion being on an opposing longitudinal side of the joint of the limb relative to the portion of the limb of the user.

10. The exoskeleton device of claim 9, further comprising a shell connected to the linear actuator, the shell being configured to form about the second portion of the limb of the user.

11. The exoskeleton device of claim 10, further comprising a strap connected to the shell and configured to secure the shell to the second portion of the limb of the user.

12. The exoskeleton device of claim 9, wherein the linear actuator is configured for securement over the second portion of the limb in parasagittal alignment with the joint of the limb of the user.

13. The exoskeleton device of claim 12, wherein the first component and the second component of the artificial joint are configured for positioning in parasagittal offset from the joint of the limb of the user.

14. The exoskeleton device of claim 9, wherein the limb is a leg of the user, and wherein the portion of the limb is a shank of the leg, and wherein the second portion of the limb is a thigh of the leg, and wherein the joint of the user is a knee of the leg.

15. The exoskeleton device of claim 14, wherein the exoskeleton device is configured for securement to a right leg of the user, and wherein the exoskeleton device is configured for securement to a left leg of the user.

16. A method for facilitating exoskeleton-assisted movement, comprising:
arranging an exoskeleton device on a user limb with an artificial joint of the exoskeleton device positioned about a joint of the user limb, wherein the artificial joint of the exoskeleton device is connected to a slider-crank mechanism powered by a linear actuator, and wherein the artificial joint comprises a first component and a second component configured for positioning on opposing lateral sides of the joint of the user limb, and wherein the slider-crank mechanism includes a four-bar mechanism that comprises (1) a first slider-crank structure connected between the linear actuator and the first component of the artificial joint, and (2) a second slider-crank structure connected between the linear actuator and the second component of the artificial joint;
applying a force to a first portion and a second portion of the user limb with the exoskeleton device, the first portion and the second portion of the user limb being on opposing longitudinal sides of the joint of the user limb; and
compensating for misalignment between the artificial joint and the joint of the user limb with a self-aligning mechanism of the exoskeleton device, the self-aligning mechanism being positioned about the first portion of the user limb, the self-aligning mechanism comprising three passive degrees of freedom (pDOF) provided in a prismatic-revolute-revolute (PRR) configuration,
wherein the compensation contributes to reduced spurious forces and/or torques exerted on the first portion of the user limb by the exoskeleton device.

17. The method of claim 16, wherein, for an assistive torque of about 50 Nm applied on the user limb by the exoskeleton device, a peak spurious force exerted on the first portion of the user limb by the exoskeleton device is below 10 N and a peak spurious torque exerted on the first portion of the user limb by the exoskeleton device is below 1 Nm.

* * * * *